US012097355B2

(12) United States Patent
Narayanaswami et al.

(10) Patent No.: US 12,097,355 B2
(45) Date of Patent: Sep. 24, 2024

(54) AUTOMATICALLY OR MANUALLY INITIATED MEAL BOLUS DELIVERY WITH SUBSEQUENT AUTOMATIC SAFETY CONSTRAINT RELAXATION

(71) Applicant: INSULET CORPORATION, Acton, MA (US)

(72) Inventors: Rangarajan Narayanaswami, Weston, MA (US); Yibin Zheng, Hartland, WI (US); Mert Sevil, Manchester, NH (US); William Whiteley, Knoxville, TN (US); Saeed Salavati, Sugar Land, TX (US); Sam Carl, Waltham, MA (US)

(73) Assignee: INSULET CORPORATION, Acton, MA (US)

( * ) Notice: Subject to any disclaimer, the term of this patent is extended or adjusted under 35 U.S.C. 154(b) by 0 days.

(21) Appl. No.: 18/390,338

(22) Filed: Dec. 20, 2023

(65) Prior Publication Data

US 2024/0226433 A1 Jul. 11, 2024

Related U.S. Application Data

(60) Provisional application No. 63/478,842, filed on Jan. 6, 2023.

(51) Int. Cl.
*A61M 5/172* (2006.01)
(52) U.S. Cl.
CPC ... *A61M 5/1723* (2013.01); *A61M 2005/1726* (2013.01); *A61M 2205/505* (2013.01); *A61M 2230/201* (2013.01)
(58) Field of Classification Search
None
See application file for complete search history.

(56) References Cited

U.S. PATENT DOCUMENTS

| 303,013 A | 8/1884 | Horton |
| 445,545 A | 2/1891 | Crane |

(Continued)

FOREIGN PATENT DOCUMENTS

| AU | 2015200834 A1 | 3/2015 |
| AU | 2015301146 A1 | 3/2017 |

(Continued)

OTHER PUBLICATIONS

US 5,954,699 A, 09/1999, Jost et al. (withdrawn)

(Continued)

*Primary Examiner* — Manuel A Mendez
(74) *Attorney, Agent, or Firm* — GOODWIN PROCTER LLP

(57) ABSTRACT

The exemplary embodiments may provide a drug delivery device that receives glucose level values for a user (e.g., a diabetic patient) and based on the glucose level values, determines when the user has consumed a meal. In some embodiments, the drug delivery device may calculate an appropriate bolus dose and automatically deliver the drug bolus to the user. In some embodiments, instead of detecting the meal, the user may announce the meal, such as by activating an element on the drug delivery device or on a management device for the drug delivery device. Responsive to the meal announcement, the drug delivery device may calculate the drug bolus dose and deliver the drug bolus. In conjunction with the delivery of the drug bolus, the drug delivery device may relax one or more safety constraints for a relaxation period following the drug bolus delivery so that additional basal drug may be delivered, if needed, under relaxed constraints.

20 Claims, 20 Drawing Sheets

(56) References Cited

U.S. PATENT DOCUMENTS

| | | |
|---|---|---|
| 588,583 A | 8/1897 | Lade |
| 1,441,508 A | 1/1923 | Marius |
| 2,283,925 A | 5/1942 | Harvey |
| 2,797,149 A | 6/1957 | Skeggs |
| 2,886,529 A | 5/1959 | Guillaud |
| 3,574,114 A | 4/1971 | Monforte |
| 3,614,554 A | 10/1971 | Shield |
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,885,662 A | 5/1975 | Schaefer |
| 3,963,380 A | 6/1976 | Thomas, Jr. et al. |
| 3,983,077 A | 9/1976 | Fuller et al. |
| 4,055,175 A | 10/1977 | Clemens et al. |
| 4,108,177 A | 8/1978 | Pistor |
| 4,146,029 A | 3/1979 | Ellinwood, Jr. |
| 4,151,845 A | 5/1979 | Clemens |
| 4,245,634 A | 1/1981 | Albisser et al. |
| 4,268,150 A | 5/1981 | Chen |
| 4,313,439 A | 2/1982 | Babb et al. |
| 4,368,980 A | 1/1983 | Aldred et al. |
| 4,373,527 A | 2/1983 | Fischell |
| 4,400,683 A | 8/1983 | Eda et al. |
| 4,403,984 A | 9/1983 | Ash et al. |
| 4,424,720 A | 1/1984 | Bucchianeri |
| 4,435,173 A | 3/1984 | Siposs et al. |
| 4,464,170 A | 8/1984 | Clemens et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A | 3/1985 | Kambara et al. |
| 4,523,170 A | 6/1985 | Huth, III |
| 4,526,568 A | 7/1985 | Clemens et al. |
| 4,526,569 A | 7/1985 | Bernardi |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,562,751 A | 1/1986 | Nason et al. |
| 4,573,968 A | 3/1986 | Parker |
| 4,585,439 A | 4/1986 | Michel |
| 4,601,707 A | 7/1986 | Albisser et al. |
| 4,624,661 A | 11/1986 | Arimond |
| 4,633,878 A | 1/1987 | Bombardieri |
| 4,634,427 A | 1/1987 | Hannula et al. |
| 4,646,038 A | 2/1987 | Wanat |
| 4,657,529 A | 4/1987 | Prince et al. |
| 4,678,408 A | 7/1987 | Nason et al. |
| 4,684,368 A | 8/1987 | Kenyon |
| 4,685,903 A | 8/1987 | Cable et al. |
| 4,731,726 A | 3/1988 | Allen, III |
| 4,743,243 A | 5/1988 | Vaillancourt |
| 4,755,169 A | 7/1988 | Sarnoff et al. |
| 4,755,173 A | 7/1988 | Konopka et al. |
| 4,759,120 A | 7/1988 | Bernstein |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,859,492 A | 8/1989 | Rogers, Jr. et al. |
| 4,880,770 A | 11/1989 | Mir et al. |
| 4,886,499 A | 12/1989 | Cirelli et al. |
| 4,898,578 A | 2/1990 | Rubalcaba, Jr. |
| 4,898,579 A | 2/1990 | Groshong et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,944,659 A | 7/1990 | Labbe et al. |
| 4,967,201 A | 10/1990 | Rich, III |
| 4,969,874 A | 11/1990 | Michel et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,007,458 A | 4/1991 | Marcus et al. |
| 5,062,841 A | 11/1991 | Siegel |
| 5,084,749 A | 1/1992 | Losee et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,130,675 A | 7/1992 | Sugawara |
| 5,134,079 A | 7/1992 | Cusack et al. |
| 5,139,999 A | 8/1992 | Gordon et al. |
| 5,153,827 A | 10/1992 | Coutre et al. |
| 5,154,973 A | 10/1992 | Imagawa et al. |
| 5,165,406 A | 11/1992 | Wong |
| 5,176,662 A | 1/1993 | Bartholomew et al. |
| 5,178,609 A | 1/1993 | Ishikawa |
| 5,189,609 A | 2/1993 | Tivig et al. |
| 5,198,824 A | 3/1993 | Poradish |
| 5,205,819 A | 4/1993 | Ross et al. |
| 5,207,642 A | 5/1993 | Orkin et al. |
| 5,213,483 A | 5/1993 | Flaherty et al. |
| 5,217,754 A | 6/1993 | Santiago-Aviles et al. |
| 5,219,377 A | 6/1993 | Poradish |
| 5,232,439 A | 8/1993 | Campbell et al. |
| 5,237,993 A | 8/1993 | Skrabal |
| 5,244,463 A | 9/1993 | Cordner, Jr. et al. |
| 5,254,096 A | 10/1993 | Rondelet et al. |
| 5,257,980 A | 11/1993 | Van Antwerp et al. |
| 5,261,882 A | 11/1993 | Sealfon |
| 5,263,198 A | 11/1993 | Geddes et al. |
| 5,272,485 A | 12/1993 | Mason et al. |
| 5,273,517 A | 12/1993 | Barone et al. |
| 5,281,202 A | 1/1994 | Weber et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,346,476 A | 9/1994 | Elson |
| 5,364,342 A | 11/1994 | Beuchat et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,403,797 A | 4/1995 | Ohtani et al. |
| 5,411,889 A | 5/1995 | Hoots et al. |
| 5,421,812 A | 6/1995 | Langley et al. |
| 5,427,988 A | 6/1995 | Sengupta et al. |
| 5,433,710 A | 7/1995 | VanAntwerp et al. |
| 5,456,945 A | 10/1995 | McMillan et al. |
| 5,468,727 A | 11/1995 | Phillips et al. |
| 5,478,610 A | 12/1995 | Desu et al. |
| 5,505,709 A | 4/1996 | Funderburk et al. |
| 5,505,828 A | 4/1996 | Wong et al. |
| 5,507,288 A | 4/1996 | Bocker et al. |
| 5,513,382 A | 4/1996 | Agahi-Kesheh et al. |
| 5,533,389 A | 7/1996 | Kamen et al. |
| 5,535,445 A | 7/1996 | Gunton |
| 5,540,772 A | 7/1996 | McMillan et al. |
| 5,543,773 A | 8/1996 | Evans et al. |
| 5,558,640 A | 9/1996 | Pfeiler et al. |
| 5,569,186 A | 10/1996 | Lord et al. |
| 5,582,593 A | 12/1996 | Hultman |
| 5,584,053 A | 12/1996 | Kommrusch et al. |
| 5,584,813 A | 12/1996 | Livingston et al. |
| 5,590,387 A | 12/1996 | Schmidt et al. |
| 5,609,572 A | 3/1997 | Lang |
| 5,614,252 A | 3/1997 | McMillan et al. |
| 5,625,365 A | 4/1997 | Tom et al. |
| 5,635,433 A | 6/1997 | Sengupta |
| 5,637,095 A | 6/1997 | Nason et al. |
| 5,665,065 A | 9/1997 | Colman et al. |
| 5,665,070 A | 9/1997 | McPhee |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |

(56) References Cited

U.S. PATENT DOCUMENTS

| | | |
|---|---|---|
| 5,703,364 A | 12/1997 | Rosenthal |
| 5,707,459 A | 1/1998 | Itoyama et al. |
| 5,707,715 A | 1/1998 | deRochemont et al. |
| 5,713,875 A | 2/1998 | Tanner, II |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,747,350 A | 5/1998 | Sattler |
| 5,747,870 A | 5/1998 | Pedder |
| 5,748,827 A | 5/1998 | Holl et al. |
| 5,755,682 A | 5/1998 | Knudson et al. |
| 5,758,643 A | 6/1998 | Wong et al. |
| 5,759,923 A | 6/1998 | McMillan et al. |
| 5,764,189 A | 6/1998 | Lohninger |
| 5,771,567 A | 6/1998 | Pierce et al. |
| 5,776,103 A | 7/1998 | Kriesel et al. |
| 5,779,676 A | 7/1998 | Kriesel et al. |
| 5,785,688 A | 7/1998 | Joshi et al. |
| 5,797,881 A | 8/1998 | Gadot |
| 5,800,397 A | 9/1998 | Wilson et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,807,075 A | 9/1998 | Jacobsen et al. |
| 5,817,007 A | 10/1998 | Fodgaard et al. |
| 5,820,622 A | 10/1998 | Gross et al. |
| 5,823,951 A | 10/1998 | Messerschmidt |
| 5,839,467 A | 11/1998 | Saaski et al. |
| 5,840,020 A | 11/1998 | Heinonen et al. |
| 5,848,991 A | 12/1998 | Gross et al. |
| 5,851,197 A | 12/1998 | Marano et al. |
| 5,854,608 A | 12/1998 | Leisten |
| 5,858,005 A | 1/1999 | Kriesel |
| 5,858,239 A | 1/1999 | Kenley et al. |
| 5,859,621 A | 1/1999 | Leisten |
| 5,865,806 A | 2/1999 | Howell |
| 5,871,470 A | 2/1999 | McWha |
| 5,879,310 A | 3/1999 | Sopp et al. |
| 5,889,459 A | 3/1999 | Hattori et al. |
| 5,891,097 A | 4/1999 | Saito et al. |
| 5,892,489 A | 4/1999 | Kanba et al. |
| 5,897,530 A | 4/1999 | Jackson |
| 5,902,253 A | 5/1999 | Pfeiffer et al. |
| 5,903,421 A | 5/1999 | Furutani et al. |
| 5,906,597 A | 5/1999 | McPhee |
| 5,911,716 A | 6/1999 | Rake et al. |
| 5,919,167 A | 7/1999 | Mulhauser et al. |
| 5,931,814 A | 8/1999 | Alex et al. |
| 5,932,175 A | 8/1999 | Knute et al. |
| 5,933,121 A | 8/1999 | Rainhart et al. |
| 5,935,099 A | 8/1999 | Peterson et al. |
| 5,945,963 A | 8/1999 | Leisten |
| 5,947,911 A | 9/1999 | Wong et al. |
| 5,957,890 A | 9/1999 | Mann et al. |
| 5,961,492 A | 10/1999 | Kriesel et al. |
| 5,965,848 A | 10/1999 | Altschul et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,019,747 A | 2/2000 | McPhee |
| 6,023,251 A | 2/2000 | Koo et al. |
| 6,024,539 A | 2/2000 | Blomquist |
| 6,027,826 A | 2/2000 | deRochemont et al. |
| 6,028,568 A | 2/2000 | Asakura et al. |
| 6,031,445 A | 2/2000 | Marty et al. |
| 6,032,059 A | 2/2000 | Henning et al. |
| 6,036,924 A | 3/2000 | Simons et al. |
| 6,040,578 A | 3/2000 | Malin et al. |
| 6,040,805 A | 3/2000 | Huynh et al. |
| 6,046,707 A | 4/2000 | Gaughan et al. |
| 6,049,727 A | 4/2000 | Crothall |
| 6,050,978 A | 4/2000 | Orr et al. |
| 6,052,040 A | 4/2000 | Hino |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,111,544 A | 8/2000 | Dakeya et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,143,432 A | 11/2000 | de Rochemont et al. |
| 6,154,176 A | 11/2000 | Fathy et al. |
| 6,157,041 A | 12/2000 | Thomas et al. |
| 6,161,028 A | 12/2000 | Braig et al. |
| 6,162,639 A | 12/2000 | Douglas |
| 6,174,300 B1 | 1/2001 | Kriesel et al. |
| 6,176,004 B1 | 1/2001 | Rainhart et al. |
| 6,181,297 B1 | 1/2001 | Leisten |
| 6,188,368 B1 | 2/2001 | Koriyama et al. |
| 6,190,359 B1 | 2/2001 | Heruth |
| 6,195,049 B1 | 2/2001 | Kim et al. |
| 6,196,046 B1 | 3/2001 | Braig et al. |
| 6,200,287 B1 | 3/2001 | Keller et al. |
| 6,200,293 B1 | 3/2001 | Kriesel et al. |
| 6,200,338 B1 | 3/2001 | Solomon et al. |
| 6,204,203 B1 | 3/2001 | Narwankar et al. |
| 6,208,843 B1 | 3/2001 | Huang et al. |
| 6,214,629 B1 | 4/2001 | Freitag et al. |
| 6,222,489 B1 | 4/2001 | Tsuru et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,266,020 B1 | 7/2001 | Chang |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,300,894 B1 | 10/2001 | Lynch et al. |
| 6,309,370 B1 | 10/2001 | Haim et al. |
| 6,312,888 B1 | 11/2001 | Wong et al. |
| 6,320,547 B1 | 11/2001 | Fathy et al. |
| 6,323,549 B1 | 11/2001 | deRochemont et al. |
| 6,334,851 B1 | 1/2002 | Hayes et al. |
| 6,363,609 B1 | 4/2002 | Pickren |
| 6,375,627 B1 | 4/2002 | Mauze et al. |
| 6,375,638 B2 | 4/2002 | Nason et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,474,219 B2 | 11/2002 | Klitmose et al. |
| 6,475,196 B1 | 11/2002 | Vachon |
| 6,477,065 B2 | 11/2002 | Parks |
| 6,477,901 B1 | 11/2002 | Tadigadapa et al. |
| 6,484,044 B1 | 11/2002 | Lilienfeld-Toal |
| 6,485,461 B1 | 11/2002 | Mason et al. |
| 6,485,462 B1 | 11/2002 | Kriesel |
| 6,491,656 B1 | 12/2002 | Morris |
| 6,492,949 B1 | 12/2002 | Breglia et al. |
| 6,496,149 B1 | 12/2002 | Birnbaum et al. |
| 6,501,415 B1 | 12/2002 | Viana et al. |
| 6,512,937 B2 | 1/2003 | Blank et al. |
| 6,520,936 B1 | 2/2003 | Mann |
| 6,525,509 B1 | 2/2003 | Petersson et al. |
| 6,527,744 B1 | 3/2003 | Kriesel et al. |
| 6,528,809 B1 | 3/2003 | Thomas et al. |
| 6,537,249 B2 | 3/2003 | Kriesell et al. |
| 6,540,260 B1 | 4/2003 | Tan |
| 6,540,672 B1 | 4/2003 | Simonsen et al. |
| 6,541,820 B1 | 4/2003 | Bol |
| 6,544,212 B2 | 4/2003 | Galley et al. |

(56) References Cited

U.S. PATENT DOCUMENTS

| | | |
|---|---|---|
| 6,546,268 B1 | 4/2003 | Ishikawa et al. |
| 6,546,269 B1 | 4/2003 | Kurnik |
| 6,552,693 B1 | 4/2003 | Leisten |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,559,735 B1 | 5/2003 | Hoang et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,115 B1 | 5/2003 | Barker et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,583,699 B2 | 6/2003 | Yokoyama |
| 6,595,956 B1 | 7/2003 | Gross et al. |
| 6,605,151 B1 | 8/2003 | Wessels et al. |
| 6,611,419 B1 | 8/2003 | Chakravorty |
| 6,618,603 B2 | 9/2003 | Varalli et al. |
| 6,620,750 B2 | 9/2003 | Kim et al. |
| 6,633,772 B2 | 10/2003 | Ford et al. |
| 6,635,958 B2 | 10/2003 | Bates et al. |
| 6,639,556 B2 | 10/2003 | Baba |
| 6,642,908 B2 | 11/2003 | Pleva et al. |
| 6,645,142 B2 | 11/2003 | Braig et al. |
| 6,650,303 B2 | 11/2003 | Kim et al. |
| 6,653,091 B1 | 11/2003 | Dunn et al. |
| 6,656,158 B2 | 12/2003 | Mahoney et al. |
| 6,662,030 B2 | 12/2003 | Khalil et al. |
| 6,669,663 B1 | 12/2003 | Thompson |
| 6,670,497 B2 | 12/2003 | Tashino et al. |
| 6,678,542 B2 | 1/2004 | Braig et al. |
| 6,680,700 B2 | 1/2004 | Hilgers |
| 6,683,576 B2 | 1/2004 | Achim |
| 6,686,406 B2 | 2/2004 | Tomomatsu et al. |
| 6,690,336 B1 | 2/2004 | Leisten et al. |
| 6,697,605 B1 | 2/2004 | Atokawa et al. |
| 6,699,218 B2 | 3/2004 | Flaherty et al. |
| 6,699,221 B2 | 3/2004 | Vaillancourt |
| 6,718,189 B2 | 4/2004 | Rohrscheib et al. |
| 6,720,926 B2 | 4/2004 | Killen et al. |
| 6,721,582 B2 | 4/2004 | Trepagnier et al. |
| 6,723,072 B2 | 4/2004 | Flaherty et al. |
| 6,727,785 B2 | 4/2004 | Killen et al. |
| 6,728,560 B2 | 4/2004 | Kollias et al. |
| 6,731,244 B2 | 5/2004 | Killen et al. |
| 6,731,248 B2 | 5/2004 | Killen et al. |
| 6,733,890 B2 | 5/2004 | Imanaka et al. |
| 6,740,059 B2 | 5/2004 | Flaherty |
| 6,740,072 B2 | 5/2004 | Starkweather et al. |
| 6,741,148 B2 | 5/2004 | Killen et al. |
| 6,742,249 B2 | 6/2004 | deRochemont et al. |
| 6,743,744 B1 | 6/2004 | Kim et al. |
| 6,750,740 B2 | 6/2004 | Killen et al. |
| 6,750,820 B2 | 6/2004 | Killen et al. |
| 6,751,490 B2 | 6/2004 | Esenaliev et al. |
| 6,753,745 B2 | 6/2004 | Killen et al. |
| 6,753,814 B2 | 6/2004 | Killen et al. |
| 6,758,835 B2 | 7/2004 | Close et al. |
| 6,762,237 B2 | 7/2004 | Glatkowski et al. |
| 6,780,156 B2 | 8/2004 | Haueter et al. |
| 6,787,181 B2 | 9/2004 | Uchiyama et al. |
| 6,791,496 B1 | 9/2004 | Killen et al. |
| 6,810,290 B2 | 10/2004 | Lebel et al. |
| 6,826,031 B2 | 11/2004 | Nagai et al. |
| 6,830,623 B2 | 12/2004 | Hayashi et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,853,288 B2 | 2/2005 | Ahn et al. |
| 6,858,892 B2 | 2/2005 | Yamagata |
| 6,862,534 B2 | 3/2005 | Sterling et al. |
| 6,864,848 B2 | 3/2005 | Sievenpiper |
| 6,865,408 B1 | 3/2005 | Abbink et al. |
| 6,871,396 B2 | 3/2005 | Sugaya et al. |
| 6,878,871 B2 | 4/2005 | Scher et al. |
| 6,883,778 B1 | 4/2005 | Newton et al. |
| 6,890,291 B2 | 5/2005 | Robinson et al. |
| 6,905,989 B2 | 6/2005 | Ellis et al. |
| 6,906,674 B2 | 6/2005 | McKinzie, III et al. |
| 6,914,566 B2 | 7/2005 | Beard |
| 6,919,119 B2 | 7/2005 | Kalkan et al. |
| 6,928,298 B2 | 8/2005 | Furutani et al. |
| 6,936,029 B2 | 8/2005 | Mann et al. |
| 6,943,430 B2 | 9/2005 | Kwon |
| 6,943,731 B2 | 9/2005 | Killen et al. |
| 6,949,081 B1 | 9/2005 | Chance |
| 6,958,809 B2 | 10/2005 | Sterling et al. |
| 6,963,259 B2 | 11/2005 | Killen et al. |
| 6,989,891 B2 | 1/2006 | Braig et al. |
| 6,990,366 B2 | 1/2006 | Say et al. |
| 7,002,436 B2 | 2/2006 | Ma et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,047,637 B2 | 5/2006 | deRochemont et al. |
| 7,060,059 B2 | 6/2006 | Keith et al. |
| 7,060,350 B2 | 6/2006 | Takaya et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,116,949 B2 | 10/2006 | Irie et al. |
| 7,128,727 B2 | 10/2006 | Flaherty et al. |
| 7,137,694 B2 | 11/2006 | Ferran et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,160,272 B1 | 1/2007 | Eyal et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,230,316 B2 | 6/2007 | Yamazaki et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,291,782 B2 | 11/2007 | Sager et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,405,698 B2 | 7/2008 | de Rochemont |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,522,124 B2 | 4/2009 | Smith et al. |
| 7,547,281 B2 | 6/2009 | Hayes et al. |
| 7,553,512 B2 | 6/2009 | Kodas et al. |
| 7,564,887 B2 | 7/2009 | Wang et al. |
| 7,569,030 B2 | 8/2009 | Lebel et al. |
| 7,595,623 B2 | 9/2009 | Bennett |
| 7,608,042 B2 | 10/2009 | Goldberger et al. |
| 7,651,845 B2 | 1/2010 | Doyle, III et al. |
| 7,652,901 B2 | 1/2010 | Kirchmeier et al. |
| 7,680,529 B2 | 3/2010 | Kroll |
| 7,714,794 B2 | 5/2010 | Tavassoli Hozouri |

(56) References Cited

U.S. PATENT DOCUMENTS

| | | | |
|---|---|---|---|
| 7,734,323 B2 | 6/2010 | Blomquist et al. |
| 7,763,917 B2 | 7/2010 | de Rochemont |
| 7,766,829 B2 | 8/2010 | Sloan et al. |
| 7,771,391 B2 | 8/2010 | Carter |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,812,774 B2 | 10/2010 | Friman et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,066,805 B2 | 11/2011 | Zurcher et al. |
| 8,069,690 B2 | 12/2011 | DeSantolo et al. |
| 8,114,489 B2 | 2/2012 | Nemat-Nasser et al. |
| 8,178,457 B2 | 5/2012 | de Rochemont |
| 8,193,873 B2 | 6/2012 | Kato et al. |
| 8,221,345 B2 | 7/2012 | Blomquist |
| 8,251,907 B2 | 8/2012 | Sterling et al. |
| 8,267,921 B2 | 9/2012 | Yodfat et al. |
| 8,350,657 B2 | 1/2013 | deRochemont |
| 8,354,294 B2 | 1/2013 | de Rochemont et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,593,819 B2 | 11/2013 | de Rochemont |
| 8,597,274 B2 | 12/2013 | Sloan et al. |
| 8,622,988 B2 | 1/2014 | Hayter |
| 8,715,839 B2 | 5/2014 | de Rochemont |
| 8,810,394 B2 | 8/2014 | Kalpin |
| 8,939,935 B2 | 1/2015 | OConnor et al. |
| 9,061,097 B2 | 6/2015 | Holt et al. |
| 9,171,343 B1 | 10/2015 | Fischell et al. |
| 9,180,244 B2 | 11/2015 | Anderson et al. |
| 9,192,716 B2 | 11/2015 | Jugl et al. |
| 9,233,204 B2 | 1/2016 | Booth et al. |
| 9,402,950 B2 | 8/2016 | Dilanni et al. |
| 9,486,571 B2 | 11/2016 | Rosinko |
| 9,520,649 B2 | 12/2016 | de Rochemont |
| 9,579,456 B2 | 2/2017 | Budiman et al. |
| 9,656,017 B2 | 5/2017 | Greene |
| 9,743,224 B2 | 8/2017 | San Vicente et al. |
| 9,857,090 B2 | 1/2018 | Golden et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0048969 A1 | 12/2001 | Constantino et al. |
| 2001/0051377 A1 | 12/2001 | Hammer et al. |
| 2001/0053895 A1 | 12/2001 | Vaillancourt |
| 2001/0056258 A1 | 12/2001 | Evans |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0047768 A1 | 4/2002 | Duffy |
| 2002/0070983 A1 | 6/2002 | Kozub et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2002/0173769 A1 | 11/2002 | Gray et al. |
| 2002/0190818 A1 | 12/2002 | Endou et al. |
| 2003/0023148 A1 | 1/2003 | Lorenz et al. |
| 2003/0034124 A1 | 2/2003 | Sugaya et al. |
| 2003/0040715 A1 | 2/2003 | DAntonio et al. |
| 2003/0050621 A1 | 3/2003 | Lebel et al. |
| 2003/0060692 A1 | 3/2003 | Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0122647 A1 | 7/2003 | Ou |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0148024 A1 | 8/2003 | Kodas et al. |
| 2003/0163097 A1 | 8/2003 | Fleury et al. |
| 2003/0170436 A1 | 9/2003 | Sumi et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2003/0221621 A1 | 12/2003 | Pokharna et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064088 A1 | 4/2004 | Gorman et al. |
| 2004/0064259 A1 | 4/2004 | Haaland et al. |
| 2004/0068224 A1 | 4/2004 | Alfred, Jr. et al. |
| 2004/0069044 A1 | 4/2004 | Lavi et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0134609 A1 | 6/2005 | Yu |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0182366 A1 | 8/2005 | Vogt et al. |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0262451 A1 | 11/2005 | Remignanti et al. |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0041229 A1 | 2/2006 | Garibotto et al. |
| 2006/0079765 A1 | 4/2006 | Neer et al. |
| 2006/0079809 A1 | 4/2006 | Goldberger et al. |
| 2006/0086994 A1 | 4/2006 | Viefers et al. |
| 2006/0100494 A1 | 5/2006 | Kroll |
| 2006/0134323 A1 | 6/2006 | OBrien |
| 2006/0134491 A1 | 6/2006 | Hilchenko et al. |
| 2006/0167350 A1 | 7/2006 | Monfre et al. |
| 2006/0173406 A1 | 8/2006 | Hayes et al. |
| 2006/0178633 A1 | 8/2006 | Garibotto et al. |
| 2006/0189925 A1 | 8/2006 | Gable et al. |

(56) References Cited

U.S. PATENT DOCUMENTS

| | | |
|---|---|---|
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0100635 A1 | 5/2007 | Mahajan et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0166453 A1 | 7/2007 | Van Duren et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0259768 A1 | 11/2007 | Kear et al. |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051738 A1 | 2/2008 | Griffin |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0114304 A1 | 5/2008 | Nalesso et al. |
| 2008/0132880 A1 | 6/2008 | Buchman |
| 2008/0160492 A1 | 7/2008 | Campbell et al. |
| 2008/0161664 A1 | 7/2008 | Mastrototaro et al. |
| 2008/0172026 A1 | 7/2008 | Blomquist |
| 2008/0172028 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2009/0326472 A1 | 12/2009 | Carter |
| 2010/0017141 A1 | 1/2010 | Campbell et al. |
| 2010/0036326 A1 | 2/2010 | Matusch |
| 2010/0057042 A1 | 3/2010 | Hayter |
| 2010/0064243 A1 | 3/2010 | Buck et al. |
| 2010/0077198 A1 | 3/2010 | Buck et al. |
| 2010/0114026 A1 | 5/2010 | Karratt |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0185183 A1 | 7/2010 | Alme et al. |
| 2010/0211003 A1 | 8/2010 | Sundar et al. |
| 2010/0228110 A1 | 9/2010 | Tsoukalis |
| 2010/0241066 A1 | 9/2010 | Hansen et al. |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0049394 A1 | 3/2011 | de Rochemont |
| 2011/0054390 A1 | 3/2011 | Searle et al. |
| 2011/0054399 A1 | 3/2011 | Chong et al. |
| 2011/0065224 A1 | 3/2011 | Bollman et al. |
| 2011/0071765 A1 | 3/2011 | Yodfat et al. |
| 2011/0098637 A1* | 4/2011 | Hill ................ A61M 5/14244 713/1 |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0124521 A1 | 5/2012 | Guo |
| 2012/0136336 A1 | 5/2012 | Mastrototaro et al. |
| 2012/0150446 A1 | 6/2012 | Chang et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0250449 A1 | 10/2012 | Nakano |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0172695 A1 | 7/2013 | Nielsen et al. |
| 2013/0172710 A1 | 7/2013 | Mears et al. |
| 2013/0178791 A1 | 7/2013 | Javitt |
| 2013/0231642 A1 | 9/2013 | Doyle et al. |
| 2013/0245545 A1 | 9/2013 | Arnold et al. |
| 2013/0253472 A1 | 9/2013 | Cabiri |

(56) References Cited

U.S. PATENT DOCUMENTS

| | | |
|---|---|---|
| 2013/0261406 A1 | 10/2013 | Rebec et al. |
| 2013/0296792 A1 | 11/2013 | Cabiri |
| 2013/0296823 A1 | 11/2013 | Melker et al. |
| 2013/0298080 A1 | 11/2013 | Griffin et al. |
| 2013/0317753 A1 | 11/2013 | Kamen et al. |
| 2013/0332874 A1 | 12/2013 | Rosinko et al. |
| 2013/0338576 A1 | 12/2013 | OConnor et al. |
| 2013/0346858 A1 | 12/2013 | Neyrinck |
| 2014/0005633 A1 | 1/2014 | Finan |
| 2014/0018730 A1 | 1/2014 | Muller-Pathle |
| 2014/0032549 A1 | 1/2014 | McDaniel et al. |
| 2014/0200426 A1 | 1/2014 | Taub et al. |
| 2014/0066886 A1 | 3/2014 | Roy et al. |
| 2014/0074033 A1 | 3/2014 | Sonderegger et al. |
| 2014/0088428 A1 | 3/2014 | Yang et al. |
| 2014/0108046 A1 | 4/2014 | Cabrera et al. |
| 2014/0121635 A1 | 5/2014 | Hayter |
| 2014/0128839 A1 | 5/2014 | Dilanni et al. |
| 2014/0129951 A1 | 5/2014 | Amin et al. |
| 2014/0135880 A1 | 5/2014 | Baumgartner et al. |
| 2014/0142508 A1 | 5/2014 | Dilanni et al. |
| 2014/0146202 A1 | 5/2014 | Boss et al. |
| 2014/0171901 A1 | 6/2014 | Langsdorf et al. |
| 2014/0180203 A1 | 6/2014 | Budiman et al. |
| 2014/0180240 A1 | 6/2014 | Finan et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0025503 A1 | 1/2015 | Searle et al. |
| 2015/0041498 A1 | 2/2015 | Kakiuchi et al. |
| 2015/0120317 A1 | 4/2015 | Mayou et al. |
| 2015/0134265 A1 | 5/2015 | Kohlbrecher et al. |
| 2015/0134353 A1 | 5/2015 | Ferrell et al. |
| 2015/0165119 A1 | 6/2015 | Palerm et al. |
| 2015/0173674 A1 | 6/2015 | Hayes et al. |
| 2015/0193585 A1 | 7/2015 | Sunna |
| 2015/0202386 A1 | 7/2015 | Brady et al. |
| 2015/0205509 A1 | 7/2015 | Scriven et al. |
| 2015/0205511 A1 | 7/2015 | Vinna et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0301691 A1 | 10/2015 | Qin |
| 2015/0306314 A1 | 10/2015 | Doyle et al. |
| 2015/0331995 A1 | 11/2015 | Zhao et al. |
| 2015/0351671 A1 | 12/2015 | Vanslyke et al. |
| 2015/0356250 A1 | 12/2015 | Polimeni |
| 2015/0366945 A1 | 12/2015 | Greene et al. |
| 2016/0015891 A1 | 1/2016 | Papiorek |
| 2016/0019352 A1 | 1/2016 | Cohen et al. |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0220181 A1 | 8/2016 | Rigooard et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0259889 A1 | 9/2016 | Murtha et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0021096 A1 | 1/2017 | Cole et al. |
| 2017/0049386 A1 | 2/2017 | Abraham et al. |
| 2017/0131887 A1 | 5/2017 | Kim et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0216524 A1* | 8/2017 | Haider .............. A61M 5/14248 |
| 2017/0239415 A1 | 8/2017 | Hwang et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0307515 A1 | 10/2018 | Meller et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0095052 A1 | 3/2019 | De Wever et al. |
| 2019/0132801 A1 | 5/2019 | Kamath et al. |
| 2019/0184091 A1 | 6/2019 | Sjolund et al. |
| 2019/0240403 A1 | 8/2019 | Palerm et al. |
| 2019/0290844 A1 | 9/2019 | Monirabbasi et al. |
| 2019/0321545 A1 | 10/2019 | Saint |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2019/0374714 A1 | 12/2019 | Rioux et al. |
| 2020/0001006 A1 | 1/2020 | Pizzochero et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0113515 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |
| 2022/0062548 A1 | 3/2022 | Zheng et al. |

FOREIGN PATENT DOCUMENTS

| | | |
|---|---|---|
| CN | 1297140 A | 5/2001 |
| CN | 101208699 A | 6/2008 |
| DE | 4200595 A1 | 7/1993 |
| DE | 19756872 A1 | 7/1999 |
| EP | 0026056 A1 | 4/1981 |
| EP | 0341049 A2 | 11/1989 |
| EP | 0496305 A2 | 7/1992 |
| EP | 0549341 A1 | 6/1993 |
| EP | 0867196 A2 | 9/1998 |
| EP | 0939451 A1 | 9/1999 |
| EP | 1177802 A1 | 2/2002 |
| EP | 1376759 A2 | 1/2004 |
| EP | 1491144 A1 | 12/2004 |
| EP | 0801578 B1 | 7/2006 |
| EP | 2139382 A1 | 1/2010 |
| EP | 2397181 A1 | 12/2011 |
| EP | 2468338 A1 | 6/2012 |
| EP | 2666520 A1 | 11/2013 |
| EP | 2695573 A2 | 2/2014 |
| EP | 2703024 A1 | 3/2014 |
| EP | 2830499 A1 | 2/2015 |
| EP | 2943149 A1 | 11/2015 |

(56) References Cited

FOREIGN PATENT DOCUMENTS

| | | |
|---|---|---|
| EP | 3177344 A1 | 6/2017 |
| EP | 3193979 A1 | 7/2017 |
| EP | 3314548 A1 | 5/2018 |
| EP | 1571582 B1 | 4/2019 |
| EP | 2897071 B1 | 5/2019 |
| EP | 3607985 A1 | 2/2020 |
| FR | 2096275 A5 | 2/1972 |
| GB | 1125897 A | 9/1968 |
| GB | 2443261 A | 4/2008 |
| JP | 51125993 A | 11/1976 |
| JP | 02131777 A | 5/1990 |
| JP | 2005326943 A | 11/2005 |
| JP | 2004283378 A | 10/2007 |
| JP | 2008513142 A | 5/2008 |
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |
| WO | 200048112 A2 | 9/1968 |
| WO | 8606796 A1 | 11/1986 |
| WO | 9800193 A1 | 1/1998 |
| WO | 9855073 A1 | 12/1998 |
| WO | 9910040 A1 | 3/1999 |
| WO | 9910049 A1 | 3/1999 |
| WO | 9956803 A1 | 11/1999 |
| WO | 9962576 A1 | 12/1999 |
| WO | 0030705 A1 | 6/2000 |
| WO | 200032258 A1 | 6/2000 |
| WO | 0172354 A2 | 10/2001 |
| WO | 2001078812 A1 | 10/2001 |
| WO | 2002015954 A1 | 2/2002 |
| WO | 0226282 A2 | 4/2002 |
| WO | 2002043866 A2 | 6/2002 |
| WO | 2002076535 A1 | 10/2002 |
| WO | 2002082990 A1 | 10/2002 |
| WO | 2003016882 A1 | 2/2003 |
| WO | 2003039362 A1 | 5/2003 |
| WO | 2003045233 A1 | 6/2003 |
| WO | 2003097133 A1 | 11/2003 |
| WO | 2004043250 A1 | 5/2004 |
| WO | 2005110601 A1 | 5/2004 |
| WO | 2004092715 A1 | 10/2004 |
| WO | 2005051170 A2 | 6/2005 |
| WO | 2005082436 A1 | 9/2005 |
| WO | 2005113036 A1 | 12/2005 |
| WO | 2006053007 A2 | 5/2006 |
| WO | 2007064835 A2 | 6/2007 |
| WO | 2007066152 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009039203 A2 | 3/2009 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2009134380 A2 | 11/2009 |
| WO | 2010022069 A2 | 2/2010 |
| WO | 2010053702 A1 | 5/2010 |
| WO | 2010077279 A1 | 7/2010 |
| WO | 2010132077 A1 | 11/2010 |
| WO | 2010138848 A1 | 12/2010 |
| WO | 2010139793 A1 | 12/2010 |
| WO | 2010147659 A2 | 12/2010 |
| WO | 2011031458 A1 | 3/2011 |
| WO | 2011075042 A1 | 6/2011 |
| WO | 2011095483 A1 | 8/2011 |
| WO | 2011133823 A1 | 10/2011 |
| WO | 2012045667 A2 | 4/2012 |
| WO | 2012073032 A1 | 6/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013050535 A2 | 4/2013 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014029416 A1 | 2/2014 |
| WO | 2014109898 A1 | 7/2014 |
| WO | 2014110538 A1 | 7/2014 |
| WO | 2014149357 A1 | 9/2014 |
| WO | 2014179774 A1 | 11/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2015117082 A1 | 8/2015 |
| WO | 2015117854 A1 | 8/2015 |
| WO | 2015167201 A1 | 11/2015 |
| WO | 2015177082 A1 | 11/2015 |
| WO | 2015187366 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017187177 A1 | 11/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2021011738 A1 | 1/2021 |
| WO | 2022081788 A1 | 4/2022 |

OTHER PUBLICATIONS

Andrenko et al., "EM Analysis of PBG Substrate Microstrip Circuits for Integrated Transmitter Front End" MMET Proceedings, 295-297 (2000).

Bardi et al., "Plane Wave Scattering From Frequency-Selective Surfaces by the Finite-Element Method" IEEE Transactions on Magnetics 38(2):641-644 (2002).

Chappell et al., "Composite Metamaterial Systems for Two-Dimensional Periodic Structures" IEEE, 3840387 (2002).

Cheng et al., "Preparation and Characterization of (Ba, Sr) TiO3 thin films using interdigitial electrodes" Microelectronic Engineering, 66:872-879 (2003).

Clavijo et al., "Design Methodology for Sievenpiper High-Impedance Surfaces: An Artificial Magnetic Conductor for Positive Gain Electrically Small Antennas" IEEE Transactions on Antennas and Propagation, 51(10):2678-2690 (2003).

Diaz et al., "Magnetic Loading of Artificial Magnetic Conductors for Bandwidth Enhancement" IEEE, 431-434 (2003).

Hansen " Effect of a High-Impedance Screen on a Dipole Antenna" IEEE Antennas and Wireless Propagation Letter, 1:46-49 (2002).

Joshi et al., "Processing and Characterization of Pure and Doped Ba0.6Sr0.4TiO3 thin films for tunable microsave applications" Mat. Res. Soc. Symp. Proc., 656E:DD4.9.1-DD4.9.6 (2001).

Kern et al., "Active Negative Impedance Loaded EBG Structures for the Realization of Ultra-Wideband Artificial Magnetic Conductors" IEEE, 427-430 (2003).

(56) References Cited

OTHER PUBLICATIONS

Kern et al., "The Synthesis of Metamaterial Ferrities for RF Applications Using Electromagnetic Bandgap Structures" IEEE, 497-500 (2003).
Kern et al., "Ultra-thin Electromagnetic Bandgap Absorbers Synthesized via Genetic Algorithms" IEEE, 1119-1122 (2003).
Kuhn et al., "Characterization of novel mono- and bifacially active semi-transparent crystalline silicon solar cells" IEEE Transactions on Electron Devices, 46(10): 2013-2017 (1999).
Kretly et al., "The Influence of the Height Variation on the Frequency Bandgap in an AMC, Artificial magnetic Conductor for Wireless Applications: an EM Experimental Design Approach" Proceedings SBMO/IEEE MTT-S IMOC, 219-223 (2003).
Lee et al., "Investigation of Electromagnetic Bandgap (EBG) Structures for Antenna Pattern Control" IEEE, 1115-1118 (2003).
McKinzie III et al., "Mitigation of Multipath Through the Use of an Artificial Magnetic Conductor for Precision CPS Surveying Antennas" IEEE, 640-643; Date of Conference: Jun. 16-21, 2002.
Monorciho et al., "Synthesis of Artificial Magnetic Conductors by Using Multilatered Frequency Selective Surfaces" IEEE Antennas and Wireless Propagation Letters, 1:196-1999 (2002).
Mosallaei et al. "Periodic Bandgap and Effective Dielectric Materials in Electromagnetics: Characterization and Applications in Nanocavities and Waveguides" IEEE Transcations on Antennas and Propagation, 51(3):549-563 (2003).
Pontes et al., "Study of the dielectric and ferroelectric properties of chemically processed BaxSr1—xTiO3 thin films" Thin Solid Films, 386(2)91-98 (2001).
Rogers et al., "AMCs Comprised of Interdigital Capacitor FSS Layers Enable Lower Cost Applications" IEEE, 411-414 (2003).
Sievenpiper et al., "Two-Dimensional Beam Steering Using an Electrically Tunable Impedance Surface" IEEE Transactions on Antennas and Propagation, 51(10):2713-2722(2003).
Sun et al., "Efficiency of Various Photonic Bandgap (PBG) Structures" 3rd Int'l. Conf. on Microwave and Millimeter Wave Technology Proceedings, 1055-1058 (2002).
Tsunemine et al., "Pt/BaxSr(1-x)TiO3/Pt Capacitor Technology for 0.15 micron Embedded Dynamic Random Access Memory" Jap. J. Appl. Phys., 43(5A):2457-2461 (2004).
Vest "Metallo-organic decomposition (MOD) processing of ferroelectric and electro-optic films: A review" Ferroelectrics, 102(1):53-68 (1990).
Viviani et al., "Positive Temperature Coefficient of Electrical Resistivity below 150k of Barium Strontium Titanate" J. Amer. Ceram. Soc. 87(4): 756-758 (2004).
Weily et al., "Antennas Based on 2-D and 3-D Electromagnetic Bandgap Materials" IEEE, 847-850 (2003).
Yang et al., "Surface Waves of Printed Antennas on Planar Artificial Periodic Dielectric Structures" IEEE Transactions on Antennas and Propagation 49(3): 444-450 (2001).
Zhang et al., "Planar Artificial magnetic Conductors and Patch Antennas" IEEE Transactions on Antennas and Propagation, 51(10):2704-2712 (2003).
Ziroff et al., "A Novel Approach for LTCC Packaging Using a PBG Structure for Shielding and Package Mode Suppression" 33rd European Microwave Conference—Munich 419-422 (2003).
International Search Report and Written Opinion for Application No. PCT/US17/61336, mailed on Jan. 25, 2018, 9 pages.
"Graph Chart." iconfinder.com. Aug. 15, 2016. Accessed Apr. 21, 2020. Available online at URL: https://www.iconfinder.com/iconsets/graph-chart-2>.
"Circular Progress Indicator Component for React." reactscript.com. Dec. 2, 2016. Accessed Sep. 9, 2020. Available online at URL: <http://reactscripts.com/circular-progress-indicator-component-react/>.
Kruska, Michal. "Circle progress bar." dribbble.com. Oct. 18, 2012. Accessed Apr. 21, 2020. Available online at URL: <https://dribbble.com/shots/775718-Circle-progress-bar>.
"C# custom control <circle progress bar) Xamarian Forms." stackoverflow.com. May 22, 2016. Accessed Apr. 21, 2020. Available online at URL: <https://stackoverflow.com/questions/37379868/c-sharp-custom-control-circle-progress-bar-xamarin-forms>.
International Search Report and Written Opinion for Application No. PCT/US2021/047685 mailed on Dec. 6, 2021, 15 pages.
International Search Report and Written Opinion for the International Patent Application No. PCT/US2021/055745, mailed Feb. 14, 2022, 13 pages.
"Circular Loader." dribbble.com. Nov. 19, 2015. Accessed Jul. 24, 2019. Available online at URL: https://dribbble.com/shots/2362441-Circular-Loader (Year: 2015).
"Creating NSSlider with 2 knobs (range slider)." stackoverflow.com. May 6, 2015. Accessed Oct. 25, 2018. Available online at URL: <https://stackoverflow.com/questions/30082809/creating-nsslider-with-2- -knobs-range-slider> (Year: 2015).
"How to do a Round Slider." freecodecamp.org. Comment from Aug. 2018. Accessed Jul. 24, 2019. Available online at URL: https://www.freecodecamp.org/forum/t/how-to-do-a-round-slider/220375 (Year: 2018).
"Tick and cross circle shape icon . . . " depositphotos.com. Aug. 27, 2016. Accessed Feb. 1, 2019. Available online at URL:<https://depositphotos.com/121291612/stock-illustration-tick-and-cross-circle-shape.html> (Year: 2016).
"Vector--Vector Illustration of Preloader / Buffer Shapes, or Dials with Knobs." 123rf.com. Accessed on Oct. 25, 2018. Available online at URL: <https://www.123rf.com/photo_37292689_stock-vector-vector-illustration- -of-preloader- buffer-shapes-or-dials-with-knobs.html>.
Gad, Tess. "Framer Cheat Sheet: Slider & Range Sliders." blog.framer.com. Jun. 12, 2017. Accessed Oct. 25, 2018. Available online at URL: <https://blog.framer.com/framer-cheat-sheets-slider-range-sliders-3dd2e5a4621d> (Year: 2017).
Obaizamomwan, Osas. "How to use the new features in iOS 9 Notes App." iphonehacks.com. Sep. 12, 2015. Accessed Apr. 24, 2018. Available online at URL: https://www.iphonehacks.com/2015/09/how-to-use-the-new-features-in-ios-9-notes-app.html.
International Search Report and Written Opinion for the International Patent Application No. PCT/US21/064056, mailed Apr. 4, 2022, 12 pages.
International Search Report and Written Opinion for the International Patent Application No. PCT/US21/064170, mailed Apr. 20, 2022, 12 pages.
Anonymous: "AndroidAPS ComponentOverview", AndroidAPS documentation, Nov. 12, 2020 (Nov. 12, 2020), pp. 1-7, Retrieved from the Internet: URL:https://github.com/openaps/AndroidAPSdocs/blob/199ef86a900adf4b3d9c32f605eb11047bd3d62f/docs/EN/Module/module.rst [retrieved on Apr. 11, 2022] the whole document.
Team Section—Qonto, by Christophe Kerebel, dated Dec. 12, 2018, dribbble.com [online]. Retrieved Jul. 1, 2022 from internet <URL: https://dribbble.com/shots/5676730-Team-Section-Qonto> (Year: 2018).
Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".
Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).
Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, mailed on Dec. 13, 2017, 8 pages.
Van Heusden et al., "Control-Relevant Models for Glucose Control using a Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).

(56) References Cited

OTHER PUBLICATIONS

Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, mailed May 16, 2017, 12 pages.
International Search Report and Written Opinion for the International Patent Application No. PCT/US2018/018901, mailed on Aug. 6, 2018, 12 pages.
International Search Report and Written Opinion for International Patent Application No. PCT/US2018/052467, mailed Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.
"Read NFC Tags with an iPHone App on iOS 11", GoToTags, Sep. 11, 2017, web <https://gototags.com/blog/read-nfc-tags-with-an-iphone-app-on-ios-11/>. (Year:2017).
International Search Report and Written Opinion for International Patent Application No. PCT/US2016/063350, mailed on Mar. 27, 2017, 9 pages.
Extended Search Report mailed Aug. 13, 2018, issued in European Patent Application No. 16753053.4, 9 pages.
International Search Report and Written Opinion for International Patent Application No. PCT/US16/18452, mailed on Apr. 29, 2015, 9 pages.
International Preliminary Report on Patentability mailed Aug. 31, 2017, issued in PCT Patent Application No. PCT/US2016/018452, 7 pages.
International Search Report and Written Opinion for International Patent Application No. PCT/US2019/055862, mailed on Mar. 11, 2020.
International Search Report and Written Opinion for Application No. PCT/US2019/030562, Sep. 25, 2019, 19 pages.
International Search Report and Written Opinion for the International Patent Application No. PCT/US2020/052125, mailed Aug. 12, 2020, 15 pages.
International Search Report and Written Opinion for the International Patent Application No. PCT/US2020/050332, mailed Sep. 12, 2020, 12 pages.
European Patent Office, "Notification of Transmittal of the ISR and the Written Opinion of the International Searching Authority, or the Declaration," in PCT Application No. PCT/GB2015/050248, Jun. 23, 2015, 12 pages.
International Search Report and Written Opinion for the International Patent Application No. PCT/US2021/012246, mailed Apr. 13, 2021, 15 pages.
International Search Report and Written Opinion for the International Patent Application No. PCT/US2021/013639, mailed Apr. 28, 2021, 14 pages.
International Search Report and Written Opinion for the International Patent Application No. PCT/US2020/063326, mailed May 3, 2021, 17 pages.
European Search Report for the European Patent Application No. 21168591, mailed Oct. 13, 2021, 4 pages.
International Search Report and Written Opinion for the International Patent Application No. PCT/US2021/041954, mailed Oct. 25, 2021, 13 pages.
International Search Report and Written Opinion for the International Patent Application No. PCT/US2021/022694, mailed Jun. 25, 2021, 13 pages.
International Search Report and Written Opinion for the International Patent Application No. PCT/US2021/017664, mailed May 26, 2021, 16 pages.
International Search Report and Written Opinion for the International Patent Application No. PCT/US2022/012896, mailed Apr. 22, 2022, 15 pages.
International Search Report and Written Opinion for the International Patent Application No. PCT/US2022/013470, mailed May 6, 2022, 14 pages.
International Search Report and Written Opinion for the International Patent Application No. PCT/US2022/013473, mailed May 6, 2022, 13 pages.
International Search Report and Written Opinion for the International Patent Application No. PCT/US2022/019079, mailed Jun. 2, 2022, 14 pages.
International Search Report and Written Opinion for the International Patent Application No. PCT/US2022/018453, mailed Jun. 2, 2022, 13 pages.
International Search Report and Written Opinion for the International Patent Application No. PCT/US22/018700, mailed Jun. 7, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI: 10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].
International Search Report and Written Opinion for the International Patent Application No. PCT/US2021/052855, mailed Dec. 22, 2021, 11 pages.

(56) References Cited

OTHER PUBLICATIONS

International Search Report and Written Opinion for the International Patent Application No. PCT/US2021/047771, mailed Dec. 22, 2021, 11 pages.
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
Turksoy Kamuran et al: "Real-time insulin 1-20 bolusing for unannounced meals with artificial pancreas", Control Engineering Practice, Pergamon Press, Oxford, GB, vol. 59, Aug. 20, 2016 (Aug. 20, 2016), pp. 159-164.
Xie Jinyu et al: "A Variable State Dimension Approach to Meal Detection and Meal Size Estimation: In Silico Evaluation Through Basal-Bolus Insulin Therapy for Type 1 Diabetes", IEEE Transactions on Biomedical Engineering, IEEE, USA, vol. 64, No. 6, Jun. 1, 2017 (Jun. 1, 2017), pp. 1249-1260 [retrieved on May 18, 2017].
Lee Seunghyun et al: "Toward a Fully Automated Artificial Pancreas System Using a Bioinspired Reinforcement Learning Design: In Silico Validation", IEEE Journal of Biomedical and Health Informatics, IEEE, Piscataway, NJ, USA, vol. 25, No. 2, Jun. 12, 2020 (Jun. 12, 2020), pp. 536-546 [retrieved on Feb. 4, 2021].
International Search Report and Written Opinion for the International Patent Application No. PCT/US2023/085081, mailed Apr. 22, 2024, 13 pages.
Unger, Jeff, et al., "Glucose Control in the Hospitalized Patient," Emerg. Med 36(9):12-18 (2004).
"Glucommander FAQ" downloaded from https://adaendo.com/GlucommanderFAQ.html on Mar. 16, 2009.
Finfer, Simon & Heritier, Stephane. (2009). The Nice-Sugar (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Search Report and Written Opinion for the International Patent Application No. PCT/US2021/016283, mailed Jun. 2, 2021, 15 pages.
Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.
Davidson, Paul C., et al., A computer-directed intravenous insulin system shown to be safe, simple, and effective in 120,618 h of operation, Diabetes Care, vol. 28, No. 10, Oct. 2005, pp. 2418-2423.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.
Gorke, A "Microbial Contamination of Haemodialysis Catheter Connections" Journal of Renal Care, European Dialysis & Transplant Nurses Association.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Schlegel et al., "Multilumen Central Venous Catheters Increase Risk for Catheter-Related Bloodstream Infection: Prospective Surveillance Study" Infection 2008; 36: 322-327.
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 mailed Jul. 16, 2010 (OPTIS. 247VPC).
International Search Report and Written Opinion in PCT/US2008/079641 (Optis.203VPC) dated Feb. 25, 2009.
Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 623-627, Feb. 1, 1998.
Billman et al., "Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved on Dec. 29, 2010 from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.
International Preliminary Report on Patentability for the International Patent Application No. PCT/US2019/053603, mailed Apr. 8, 2021, 9 pages.
International Search Report and Written Opinion for the International Patent Application No. PCT/US2019/053603, mailed Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech, vol. Diabetes Technology Society ;(5): 1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).

(56) References Cited

OTHER PUBLICATIONS

Anonymous: "Fuzzy control system", Wikipedia, Jan. 10, 2020. URL: https://en.wikipedia.org/w/index.php?title=Fuzzy_control_system&oldid=935091190.

An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.

International Search Report and Written Opinion for the InternationalPatent Application No. PCT/US2021/017441, mailed May 25, 2021, 12 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, mailed May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, mailed May 27, 2021, 16 pages.

International Search Report and Written Opinion for the International Patent Application No. PCT/US2020/065226, mailed May 31, 2021, 18 pages.

International Search Report and Written Opinion for the International Patent Application No. PCT/US2021/017659, mailed May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

* cited by examiner

AUTOMATICALLY OR MANUALLY INITIATED MEAL BOLUS DELIVERY WITH SUBSEQUENT AUTOMATIC SAFETY CONSTRAINT RELAXATION

RELATED APPLICATIONS

This application claims the benefit of U.S. Provisional Patent Application No. 63/478,842, filed Jan. 6, 2023, the entire contents of which are incorporated herein by reference in its entirety.

BACKGROUND

Diabetic patients need additional insulin to offset the rise in glucose levels that follows consumption of a meal. Traditionally, such diabetic patients have delivered insulin boluses via manual injections in anticipation of consuming meals. The diabetic patients must determine the doses for the insulin boluses. This can be difficult and prone to error. The diabetic patients must correctly determine the amount of carbohydrates in the meals and must correctly determine the proper insulin bolus doses to offset the rise in glucose levels that will result from consuming the calculated amounts of carbohydrates for the meals. The diabetic patients also must time the delivery of the insulin bolus properly relative to consuming the meals. Sometimes diabetic patients may even forget to deliver an insulin bolus for a meal. The net result often is poor glucose level management. Diabetic patients may become hyperglycemic as a result of choosing insulin boluses that are too small or may become hypoglycemic by choosing insulin boluses that are too large.

SUMMARY

In accordance with a first inventive facet, a drug delivery system for delivery of a drug, such as insulin, to a user may include a storage or reservoir for the drug and a needle and/or cannula for piercing the skin of the user to deliver the drug from the storage. The drug delivery system may further include a fluid path for the drug between the storage to the needle or cannula and a non-transitory computer-readable storage medium storing computer programming instructions and other historical information. The drug delivery system may additionally include a processor configured to execute the computer programming instructions. Executing the computer programming instructions may cause the processor to constrain delivery of the drug to the, receive glucose level values for the user, and/or other analyte level values, and determine whether the user has eaten based on the received analyte level values for the user. Executing the computer programming instruction also may cause the processor to provide an auto bolus capability to deliver a first portion of a drug bolus to the user responsive to the processor determining that the user has eaten, and relax at least one of the drug safety constraints for a period following the delivery of the first portion of the drug bolus so that larger doses of basal drug deliveries may be delivered if needed without being subject to the at least one drug safety constraints that were relaxed.

The executing of the computer programming instructions may further cause the processor to deliver a second portion of the drug bolus. Executing the computer programming instructions may further cause the processor to determine a dose for the second portion of the drug bolus. The second portion of the dose may be determined based at least in part on a most recent received analyte level value and drug on board for the user. Executing the computer programming instructions may further cause the processor to prevent delivery of another drug bolus during a cool down period following delivery of the second portion of the drug bolus. The executing of the computer programming instructions may further cause the processor to cancel the auto bolus capability if an activity mode is set wherein the activity mode being set indicates that the user is active or going to be active shortly or if the user is in the cool down period. The executing of the computer programming instructions may further cause the processor to cancel the relaxing of the at least one drug delivery constraint if at least one cancelation condition other than the expiration of the period is satisfied. The cancelation condition(s) may include at least one of a difference between consecutively received blood glucose values for the user that exceeds a threshold or an activity mode is set wherein the activity mode being set indicates that the user is active or going to be active shortly.

In accordance with another inventive facet, a method configured to be executed on or performed by a processor of a drug delivery system may comprise receiving glucose level values for the user, and/or other analyte level values, and determining whether the user has eaten based on the received analyte level values for the user. The method may further comprise an auto bolus capability to determine a first portion of a drug bolus to be delivered to the user responsive to the method determining that the user has eaten, determining that the drug delivery system has delivered the first portion to the user, and relaxing at least one drug safety constraint for a period following the determination that the first portion of the drug bolus has been delivered, wherein relaxing the at least one drug safety constraint allows determination of larger doses of basal drug deliveries to be delivered if needed without being subject to the at least one drug safety constraints that were relaxed.

The method may further comprise determining a dose for the second portion of the drug bolus to be delivered to the user. The second portion of the dose may be determined based at least in part on a most recent received analyte level value and drug on board for the user. The method may further comprise determining that the second portion of the drug bolus has been delivered. Additionally, the method may further comprise preventing delivery of another drug bolus during a cool down period following the determination that the second portion of the drug bolus has been delivered and/or sending instructions to the drug delivery device indicating that another drug bolus shall not be delivered within the cool down period following the determination that the second portion of the drug bolus has been delivered. The method may further comprise canceling the auto bolus capability if an activity mode is set wherein the activity mode being set indicates that the user is active or going to be active shortly or if the user is in the cool down period. The method may further cause the processor to cancel the relaxing of the at least one drug delivery constraint if at least one cancelation condition other than the expiration of the period is satisfied. The cancelation condition(s) may include at least one of a difference between consecutively received blood glucose values for the user that exceeds a threshold or an activity mode is set wherein the activity mode being set indicates that the user is active or going to be active shortly.

In accordance with another inventive facet, a drug delivery system for delivery of drug to a user may include a storage or reservoir of drug such as insulin and a needle and/or cannula for piercing the skin of the user to deliver the drug from the storage. The drug delivery system may further include a fluid path for the drug between the storage to the needle or cannula. The drug delivery system may include a non-transitory computer-readable storage medium storing historical information and computer programming instructions and a processor configured to execute the computer programming instructions. Executing the computer programming instructions may cause the processor to constrain delivery of the drug to the user per current drug safety constraints and to receive an indication of a user request to deliver a drug bolus immediately to the user. The executing of the computer programming instructions may further cause the processor to, responsive to the received request, deliver a first portion of the drug bolus to the user, and relax at least one of the current drug safety constraints for a period following the delivery of the first portion of the drug bolus so that larger doses of basal drug deliveries may be delivered if needed without being subject to the at least one of the current drug safety constraints that were relaxed.

The drug delivery system may include an element that may be activated by the user to request delivery of the drug bolus. The element may be, for example, one of a button, a knob, a switch, a lever, or a user interface element. The executing of the computer programming instructions may further cause the processor to deliver a second portion of the drug bolus. The executing of the computer programming instructions may further cause the processor to determine a dose for the second portion of the drug bolus. The executing of the computer programming instructions may further cause the processor to prevent delivery of another drug bolus during a cool down period following delivery of the second portion of the drug bolus. The executing of the computer programming instructions may further cause the processor to cancel the relaxing of the at least one drug safety constraint if differences between consecutively received blood glucose values for the user exceed respective thresholds or if an activity mode is set wherein the activity mode being set indicates that the user is active or going to be active shortly.

In accordance with an additional inventive facet, a method configured to be executed on or performed by a processor of a drug delivery system may comprise receiving an indication of a user request to deliver a drug bolus immediately to the user. The method may further comprise responsive to the received request, determine a first portion of the drug bolus to be delivered the user, determining that the first portion of the drug bolus has been delivered by the drug delivery system and relax at least one of a current drug safety constraint for a period following the delivery of the first portion of the drug bolus, wherein relaxing the at least one drug safety constraint allows determination of larger doses of basal drug deliveries to be delivered if needed without being subject to the at least one drug safety constraints that were relaxed.

In accordance with an additional inventive facet, a drug delivery device includes a drug reservoir storing a drug such as insulin and a needle and/or cannula for piercing skin of a patient, said needle and/or cannula being hollow so as to serve as a conduit for delivering drug to the user. The drug delivery device may include a non-transitory computer-readable storage storing computer programing instructions for controlling operation of the drug delivery device. The drug delivery device may include a processor for executing the computer programming instructions to cause the processor to constrain delivery of the drug to the user per current drug delivery constraints, deliver a first portion of the drug bolus to the user, and relax at least one of the current drug safety constraints for a period following the delivery of the first portion of the drug bolus so that larger doses of basal drug deliveries may be delivered if needed without being subject to the at least one current drug safety constraints that were relaxed.

In accordance with an additional inventive facet, a method configured to be executed on or performed by a processor of a drug delivery system may comprise determining a first portion of a drug bolus to be delivered the user, determine that the first portion of a drug bolus has been delivered by the drug delivery system and relax at least one of the current drug safety constraints for a period following the delivery of the first portion of the drug bolus, wherein relaxing the at least one drug safety constraint allows determination of larger doses of basal drug deliveries to be delivered if needed without being subject to the at least one drug safety constraints that were relaxed.

Multiple of the current drug safety constraints may be relaxed. The drug safety constraints may include at least one of a maximum amount of drug that can be delivered to the user from the drug delivery device in an operational cycle of the drug delivery device, a maximum amount of drug that can be delivered to the user from the drug delivery device in a specified number of operational cycles of the drug delivery device, a setpoint for glucose or other analyte level of the user, a maximum level of drug on board for the user, and a penalty amount in a cost function for extra drug delivery. The executing of the computer programming instructions may further cause the processor to deliver a second portion of the drug bolus at a fixed time after delivery of the first portion of the drug bolus. The method may further comprise determining a second portion of the drug bolus to be delivered to the user at a fixed time after delivery of the first portion of the drug bolus.

DETAILED DESCRIPTION

The exemplary embodiments may reduce the burden on diabetic patients regarding delivery of meal boluses of drug such as insulin. The exemplary embodiments may provide a drug delivery device and/or drug delivery system that receives glucose and/or other analyte level values for a user (e.g., a diabetic patient or person with diabetes (PWD)) and based on the glucose or other analyte level values, determine when the user has consumed a meal. In some embodiments, the drug delivery device and/or drug delivery system may calculate an appropriate bolus dose and automatically deliver the drug bolus to the user. Thus, the user is relieved of the burden of remembering to deliver a drug bolus for a meal and also is relieved of correctly determining the drug bolus dose. In some embodiments, instead of detecting the meal, the user may announce the meal, such as by activating an element on the drug delivery device or on a management device for the drug delivery device, e.g. wherein the management device is part of the drug delivery system. Responsive to the meal announcement, the drug delivery device may calculate the drug bolus dose and deliver the drug bolus.

In conjunction with the delivery of the drug bolus, the drug delivery device may relax safety constraints for a relaxation period following the drug bolus delivery so that additional basal drug may be delivered if needed. The drug bolus dose may be chosen to be conservative (i.e., a dose that may be less than needed to fully respond to the meal consumption) to reduce the risk of the user becoming hypoglycemic. The drug delivery device may rely upon the relaxed safety constraints to enable more aggressive basal drug delivery to complete the compensation needed to bring glucose levels of the user into a desirable range following meal consumption. The relaxation period may be canceled if glucose level trends indicate a substantial decreasing trend or if the user enters a mode indicating that the user is active, such as exercising. In some embodiments, relaxing the safety constraints allows the drug delivery system or device to deliver a higher amount of basal insulin.

The exemplary embodiments may provide a cool down phase wherein an additional drug bolus may not be delivered in a period following delivery of a drug bolus despite a meal being detected or the user announcing a meal.

The exemplary embodiments may accommodate both the automatic bolus delivery responsive to meal detection with safety constraint relaxation and the bolus delivery responsive to a user meal announcement with safety constraint relaxation. The exemplary embodiments may provide measures to resolve conflicts that may arise with the automatic bolus delivery and meal announcement. The drug delivery device may intelligently halt relaxation of the safety constraints and/or meal detection as needed.

Figure 1:
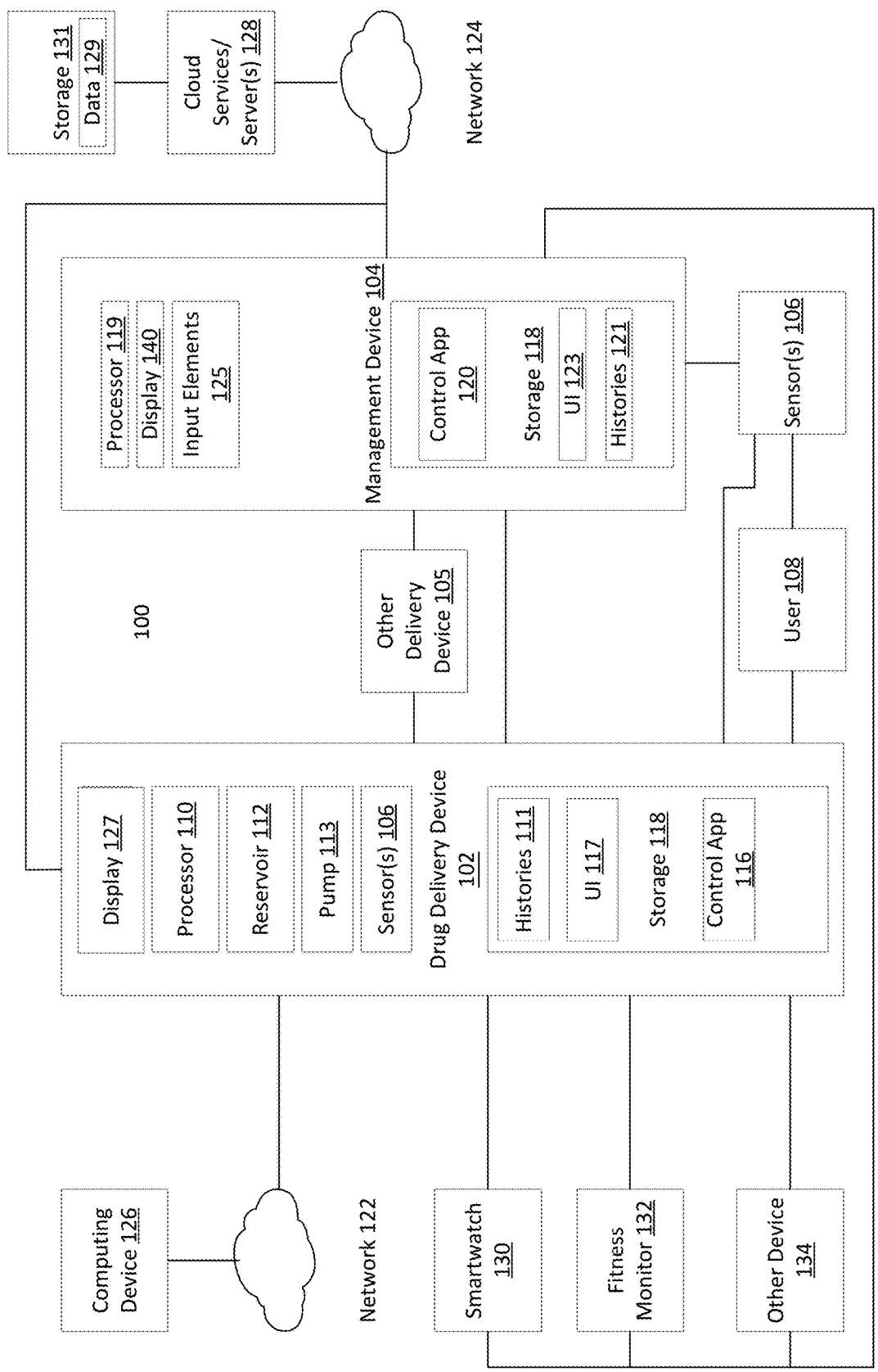
FIG. 1 depicts a block diagram of a drug delivery system of exemplary embodiments.

FIG. 1 depicts a block diagram of an illustrative drug delivery system 100 that is suitable for delivering a drug such as insulin to a user 108 in accordance with the exemplary embodiments. The drug delivery system 100 includes a drug delivery device 102. The drug delivery device 102 may be a wearable device that is worn on the body of the user 108 or carried by the user. The drug delivery device 102 may be directly coupled to a user (e.g., directly attached to a body part and/or skin of the user 108 via an adhesive or the like) with no tubes and an infusion location directly under the drug delivery device 102, or carried by the user (e.g., on a belt or in a pocket) with the drug delivery device 102 connected to an infusion site where the drug is injected using a needle and/or cannula. A surface of the drug delivery device 102 may include an adhesive to facilitate attachment to the user 108.

The drug delivery device 102 may include a processor 110. The processor 110 may be, for example, a microprocessor, a logic circuit, a field programmable gate array (FPGA), an application specific integrated circuit (ASIC) or a microcontroller. The processor 110 may maintain a date and time as well as other functions (e.g., calculations or the like). The processor 110 may be operable to execute a control application 116 encoded in computer programming instructions stored in the storage 114 that enables the processor 110 to direct operation of the drug delivery device 102. The control application 116 may be a single program, multiple programs, modules, libraries or the like. The processor 110 also may execute computer programming instructions stored in the storage 114 for a user interface (UI) 117 that may include one or more display screens shown on display 127. The display 127 may display information to the user 108 and, in some instances, may receive input from the user 108, such as when the display 127 is a touchscreen.

The control application 116 may control delivery of the drug to the user 108 per a control approach like that described herein. In exemplary embodiments, the control application 116 may control the termination of the electric pulse to an SMA (Shape Memory Alloy) element as described below. The storage 114 may hold histories 111 for a user, such as a history of basal deliveries, a history of bolus deliveries, and/or other histories, such as a meal event history, exercise event history, glucose level history, other analyte level history, and/or the like. In addition, the processor 110 may be operable to receive data or information. The storage 114 may include both primary memory and secondary memory. The storage 114 may include random access memory (RAM), read only memory (ROM), optical storage, magnetic storage, removable storage media, solid state storage or the like.

The drug delivery device 102 may include a tray or cradle and/or one or more housings for housing its various components including a pump 113, a power source (not shown), and a reservoir 112 for storing drug for delivery to the user 108. A fluid path to the user 108 may be provided, and the drug delivery device 102 may expel the drug from the reservoir 112 to deliver the drug to the user 108 using the pump 113 via the fluid path. The fluid path may, for example, include tubing coupling the drug delivery device 102 to the user 108 (e.g., tubing coupling a cannula to the reservoir 112), and may include a conduit to a separate infusion site. The drug delivery device 102 may have operational cycles, such as every 5 minutes, in which basal doses of drug are calculated and delivered as needed. These steps are repeated for each cycle.

There may be one or more communications links with one or more devices physically separated from the drug delivery device 102 including, for example, a management device 104 of the user and/or a caregiver of the user, sensor(s) 106, a smartwatch 130, a fitness monitor 132 and/or another variety of device 134. The communication links may include any wired or wireless communication links operating according to any known communications protocol or standard, such as Bluetooth®, Wi-Fi, a near-field communication standard, a cellular standard, or any other wireless protocol.

The drug delivery device 102 may interface with a network 122 via a wired or wireless communications link. The network 122 may include a local area network (LAN), a wide area network (WAN), a cellular network, a Wi-Fi network, a near field communication network, or a combination thereof. A computing device 126 may be interfaced with the network 122, and the computing device may communicate with the drug delivery device 102.

The drug delivery system 100 may include one or more sensor(s) 106 for sensing the levels of one or more analytes. The sensor(s) 106 may be coupled to the user 108 by, for example, adhesive or the like and may provide information or data on one or more medical conditions and/or physical attributes of the user 108. The sensor(s) 106 may be physically separate from the drug delivery device 102 or may be an integrated component thereof. The sensor(s) 106 may include, for example, glucose monitors, such as continuous glucose monitors (CGM's) and/or non-invasive glucose monitors. The sensor(s) 106 may include ketone sensors, other analyte sensors, heart rate monitors, breathing rate monitors, motion sensors, temperature sensors, perspiration sensors, blood pressure sensors, alcohol sensors, or the like. Some sensors 106 may also detect characteristics of components of the drug delivery device 102. For instance, the sensors 106 in the drug delivery device may include voltage sensors, current sensors, temperature sensors and the like.

The drug delivery system 100 may or may not also include a management device 104. In some embodiments, no management device is needed as the drug delivery device 102 may manage itself. The management device 104 may be a special purpose device, such as a dedicated personal diabetes manager (PDM) device. The management device 104 may be a programmed general-purpose device, such as any portable electronic device including, for example, a dedicated controller, such as a processor, a micro-controller, or the like. The management device 104 may be used to program or adjust operation of the drug delivery device 102 and/or the sensor(s) 106. The management device 104 may be any portable electronic device including, for example, a dedicated device, a smartphone, a smartwatch, or a tablet. In the depicted example, the management device 104 may include a processor 119 and a storage 118. The processor 119 may execute processes to manage a user's glucose levels and to control the delivery of the drug to the user 108. The drug delivery device 102 may provide data from the sensors 106 and other data to the management device 104. The data may be stored in the storage 118. The processor 119 may also be operable to execute programming code stored in the storage 118. For example, the storage 118 may be operable to store one or more control applications 120 for execution by the processor 119. Storage 118 may also be operable to store historical information such as drug delivery information, analyte level information, user input information, output information, or other historical information. The control application 120 may be responsible for controlling the drug delivery device 102, such as by controlling the automated drug delivery (ADD) (or, for example, automated insulin delivery (AID)) of drug to the user 108. In some exemplary embodiments, the control application 120 provides the adaptability described herein. The storage 118 may store the control application 120, histories 121 like those described above for the drug delivery device 102, and other data and/or programs. The embodiments presented herein may also be performed by a plurality of processors for example in a distributed computer system.

A display 140, such as a touchscreen, may be provided for displaying information. The display 140 may display user interface (UI) 123. The display 140 also may be used to receive input, such as when it is a touchscreen. The management device 104 may further include input elements 125, such as a keyboard, button, knobs, or the like, for receiving input form the user 108.

The management device 104 may interface with a network 124, such as a LAN or WAN or combination of such networks, via wired or wireless communication links. The management device 104 may communicate over network 124 with one or more servers or cloud services 128. Data, such as sensor values, may be sent, in some embodiments, for storage and processing from the drug delivery device 102 directly to the cloud services/server(s) 128 or instead from the management device 104 to the cloud services/server(s) 128.

Other devices, like smartwatch 130, fitness monitor 132 and device 134 may be part of the drug delivery system 100. These devices 130, 132 and 134 may communicate with the drug delivery device 102 and/or management device 104 to receive information and/or issue commands to the drug delivery device 102. These devices 130, 132 and 134 may execute computer programming instructions to perform some of the control functions otherwise performed by processor 110 or processor 119, such as via control applications 116 and 120. These devices 130, 132 and 134 may include displays for displaying information. The displays may show a user interface for providing input by the user, such as to request a change or pause in dosage, or to request, initiate, or confirm delivery of a bolus of drug, or for displaying output, such as a change in dosage (e.g., of a basal delivery amount) as determined by processor 110 or management device 104. These devices 130, 132 and 134 may also have wireless communication connections with the sensor 106 to directly receive analyte measurement data. Another delivery device 105, such as a drug delivery pen (such as an insulin pen), may be accounted for (e.g., in determining IOB) or may be provided for also delivering drug to the user 108.

The functionality described herein for the exemplary embodiments may be under the control of or performed by the control application 116 of the drug delivery device 102 or the control application 120 of the management device 104. In some embodiments, the functionality wholly or partially may be under the control of or performed by the cloud services/servers 128, the computing device 126 or by the other enumerated devices, including smartwatch 130, fitness monitor 132 or another wearable device 134.

In the closed loop mode, the control application 116, 120 determines the drug delivery amount for the user 108 on an ongoing basis based on a feedback loop. For a drug delivery device that uses insulin, for example, the aim of the closed loop mode is to have the user's glucose level at a target glucose level or within a target glucose range. In some embodiments, the target glucose level is between about 100 mg/dL to about 140 mg/dL, more specifically between about 110 mg/dL to about 130 mg/dL and in particular between about 115 mg/dL to about 120 mg/dL.

In some embodiments, the drug delivery device 102 need not deliver one drug alone. Instead, the drug delivery device 102 may one drug, such as insulin, for lowering glucose levels of the user 108 and also deliver another drug, such as glucagon, for raising glucose levels of the user 108. The drug delivery device 102 may deliver a glucagon-like peptide (GLP)-1 receptor agonist drug for lowering glucose concentration in the blood or slowing gastric emptying, thereby delaying spikes in glucose after a meal. In other embodiments, the drug delivery device 102 may deliver pramlintide, or other drugs that may substitute for insulin. In other embodiments, the drug delivery device 102 may deliver concentrated insulin. In some embodiments, the medicament or drug delivered by the drug delivery device may be a coformulation of two or more of those medicaments identified above. In a preferred embodiment, the drug delivery device delivers insulin; accordingly, reference will be made throughout this application to insulin and an insulin delivery device, but one of ordinary skill in the art would understand that drugs other than insulin can be delivered in lieu of or in addition to insulin.

Figure 2:
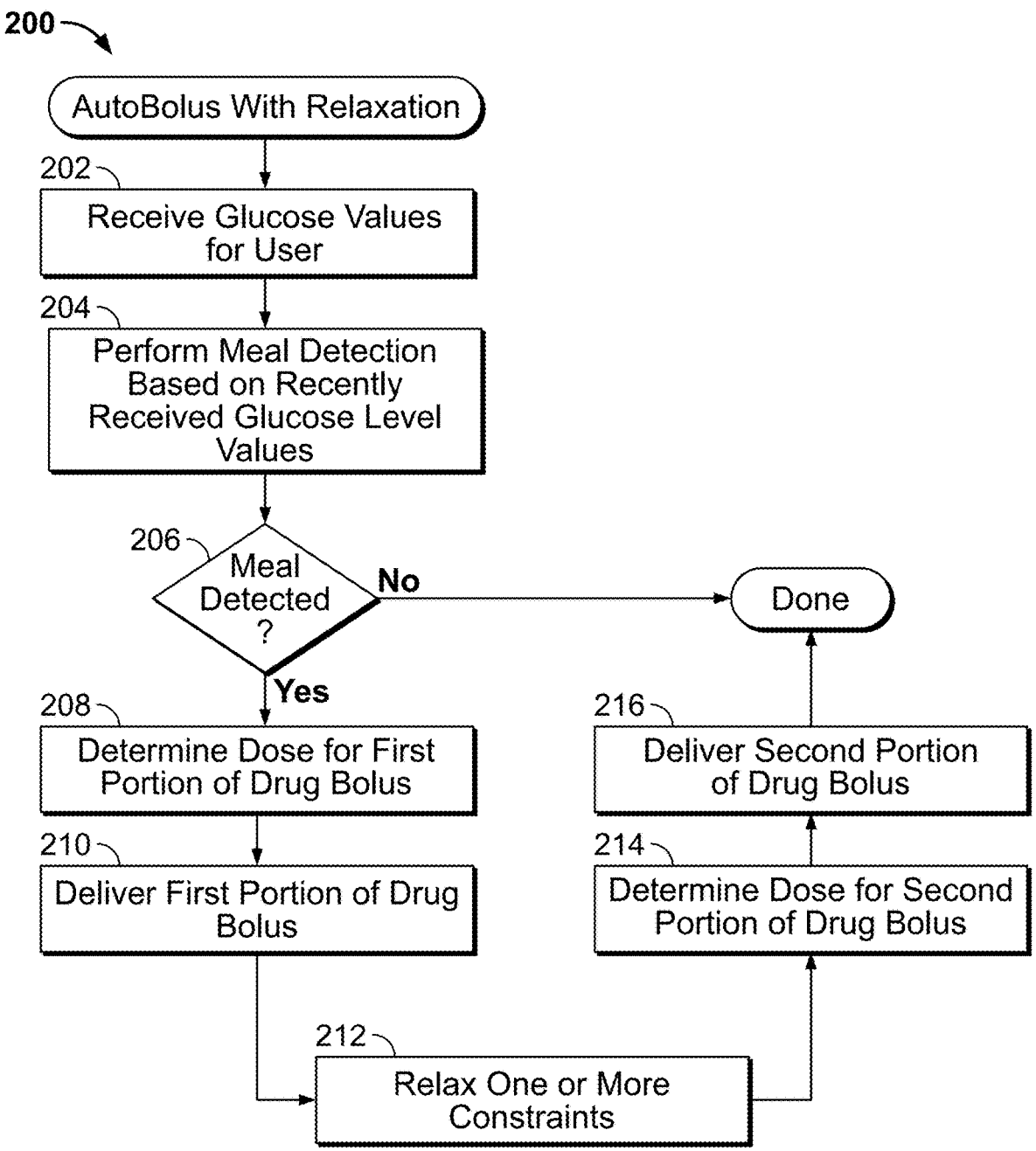
FIG. 2 depicts a flowchart of illustrative steps that may be performed in exemplary embodiments with an AutoBolus capability.

As mentioned above, the exemplary embodiments may automatically detect meal ingestion by a user 108 based on glucose level values, and automatically deliver an insulin bolus to offset the rise in glucose due to the ingestion of the meal. The automatic delivery of the bolus may be referred to herein as "AutoBolus." FIG. 2 depicts a flowchart 200 of illustrative steps that may be performed in exemplary embodiments in providing the AutoBolus capability. At 202, glucose level values are received for the user. The glucose level values may originate from a glucose sensor, such as a CGM, that is one of the sensor(s) 106. Where the glucose level values originate from a CGM, the glucose values may be received via a wireless connection between the CGM and the drug delivery device 102. The glucose level values may be sent through an intermediate device, like the management device 104, on their way to the drug delivery device 102. Moreover, the glucose level values may be stored in storage 118 and retrieved from the storage 118 as needed. The glucose level values may be the most recent ones obtained for the user 100 and may include enough values to detect meals as is explained below (e.g., glucose level values for rolling 15 minute windows). Alternatively, the glucose level values may be obtained from a glucometer that reads test strips on which a drop of the user's blood has been applied or from another variety of glucose sensor. The most recent glucose level value may be the glucose level values received closest to the current time, e.g. wherein the current time is the point in time where the automatic meal detection takes place.

Figure 3A:
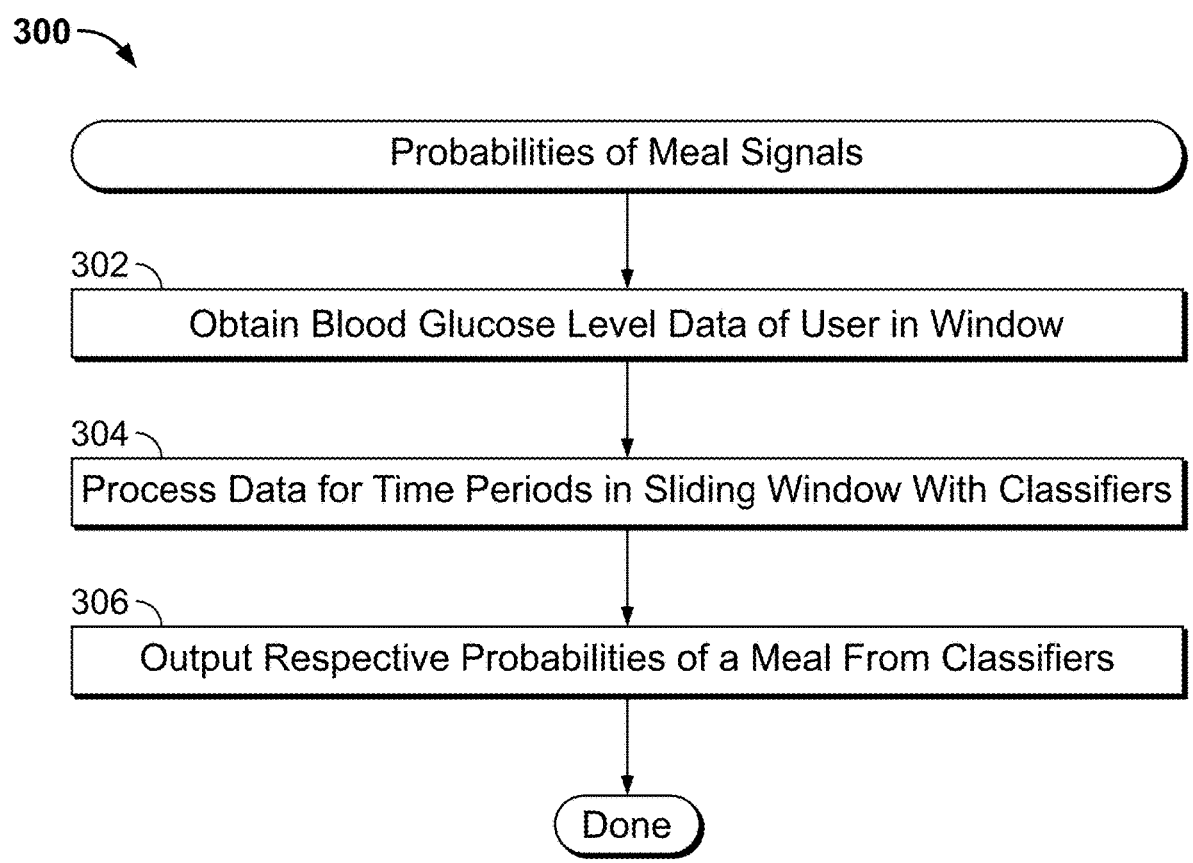
FIG. 3A depicts a flowchart of illustrative steps that may be performed in exemplary embodiments to obtain meal signals for automatic meal detection.

At 204, the glucose level values are processed to detect whether the user 108 has ingested a meal. The exemplary embodiments may gather meal signals based on glucose level values from the user over a time window and use the meal signals to determine if a meal has been detected or not at 203. The meal signals represent probabilities that a meal has been detected in glucose level values for the user 108 at successive time intervals. FIG. 3A depicts a flowchart 300 of illustrative steps that may be performed in exemplary embodiments to obtain the meal signals. In accordance with this approach during training of the machine learning model for meal detection, glucose rises of specified or predetermined magnitudes within respective time periods are sought. For example, the approach may look for instances of a 20 mg/dL rise or greater within a 15-minute period, a 40 mg/dL rise or greater in a 30-minute period and a 60 mg/dL rise or greater in a 60-minute period. As an embodiment in model prediction mode, limited data from 10 minutes, 15 minutes and 20 minutes of glucose values are used to predict if the glucose is going to rise in the next 30 minutes to 60 minutes time frame. At 302, blood glucose level data of the user 108 is obtained for 10-minute periods, 15-minute periods and 20-minute periods within a window, such as a two-hour window, ending with a most recent glucose level reading. In some embodiments, the glucose values of the prior about 5 minutes to about 40 minutes (relative to the current time), more specifically the glucose values of the prior about 10 minutes to about 30 minutes and in particular of the prior 10 minutes to about 20 minutes are used to predict if the glucose is going to rise in the next 30 minutes to 60 minutes time frame.

In the exemplary embodiments, at 304, classifiers may process the glucose level values to predict glucose level rises using glucose values in 10 minute, 15 minute and 20 minute time windows. A separate classifier may be provided for each time period. The classifiers may be machine learning models that recognize patterns of glucose level rises indicative of meals. The classifiers may be part of the control application 116 or 120. One classifier may utilize glucose values in a 10-minute interval in the window. Another classifier may utilize glucose values in a 15-minute interval in the window, and a third classifier may utilize glucose values in a 20 minute interval in the window. Each classifier may be, for example, a separate neural network model or a separate decision tree model. The classifiers may output the probability that a meal has been detected within the window based on computed features in the time window such as first and second derivative, mean values, range values in the window, etc. While the 10 minute, 15 minute and 20 minute time windows for predicting glucose rise probabilities are used as exemplary embodiments, it should be noted that larger windows that utilize more glucose values for example, 30 minute, 60 minute, 120 minute windows are other possible embodiments, for example.

At 306, the classifiers may output their respective probabilities, which are used in determining probabilities of whether there has been a meal event, and in determining the maximum allowed insulin bolus dose, as described above. The monitoring of the glucose level data of the user 108 may be performed on an ongoing basis.

Figure 3B:
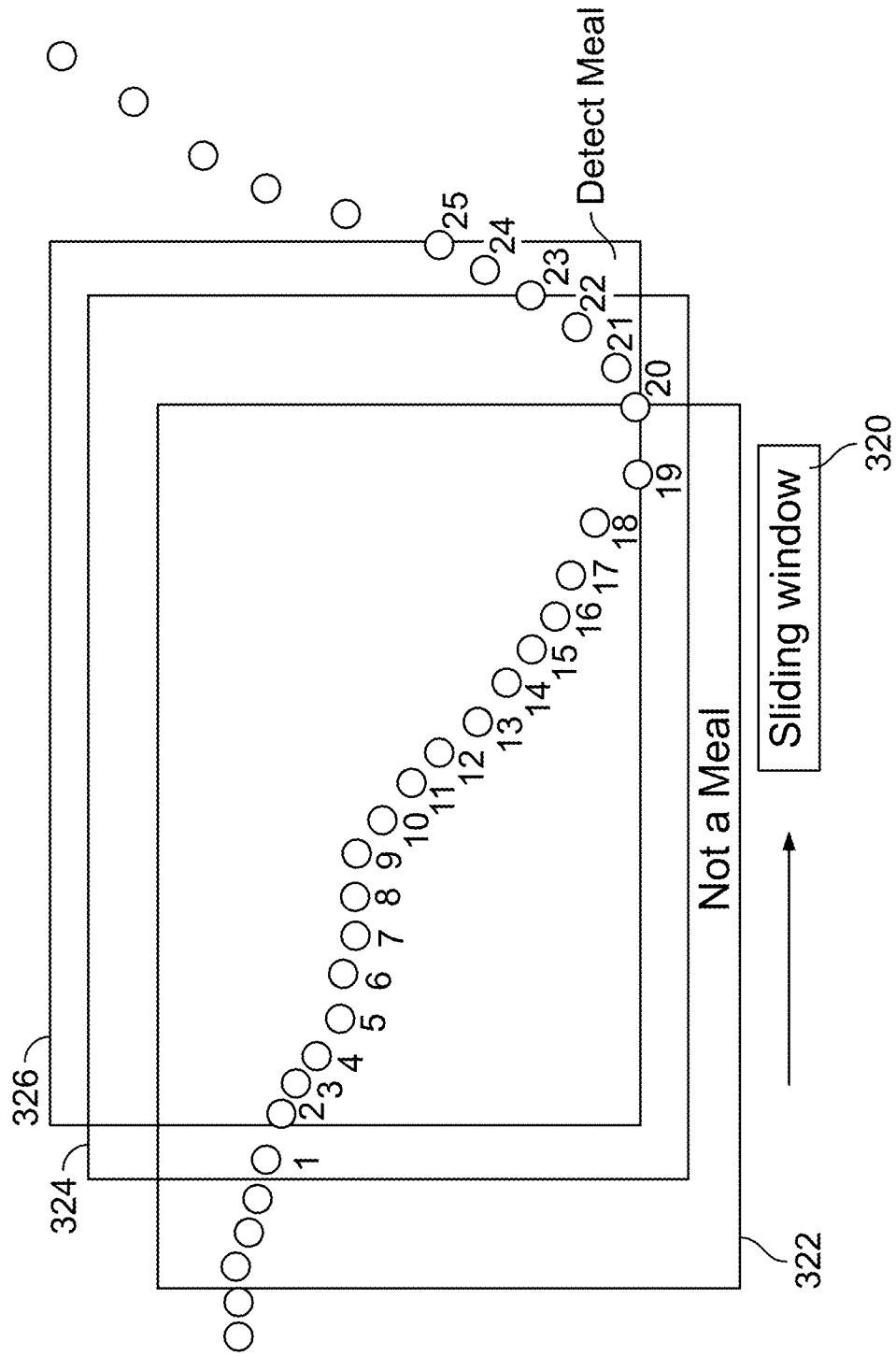
FIG. 3B depicts an example sliding window that slides over time to encompass an updated two-hour period as new glucose level readings are received for meal detection in exemplary embodiments.

FIG. 3B depicts an example sliding window 320 that slides over time to encompass an updated two-hour period as new glucose level readings are received. The sliding window 320 may start off in position or window 322 that covers glucose level readings up to reading number 20. In a second position or window 324, the window encompasses readings from reading 1 to reading 23, and in the third position or window 326, the window encompasses from reading 2 to reading 25. Each reading may occur at 5-minute intervals; thus, one window may encompass a two-hour period. In positions of windows or positions 322 and 324, no meal is detected, but a meal is detected in position or window 326 based on the predicted glucose level rise.

With reference to FIG. 2, at 206, a check may be made whether a meal is detected based on the glucose level values. If not, the process of FIG. 2 is complete. If so, at 208, a dose for a first portion of the insulin bolus may be determined. In the exemplary embodiments, a first portion of the insulin bolus may be delivered by the AutoBolus mechanism immediately after the meal is detected. This may be followed by the delivery of a second portion of the insulin bolus, such as during a next operational cycle, as is explained below. The dose for the first portion of the insulin bolus may be chosen to be a safe amount to be delivered immediately.

Figure 4:
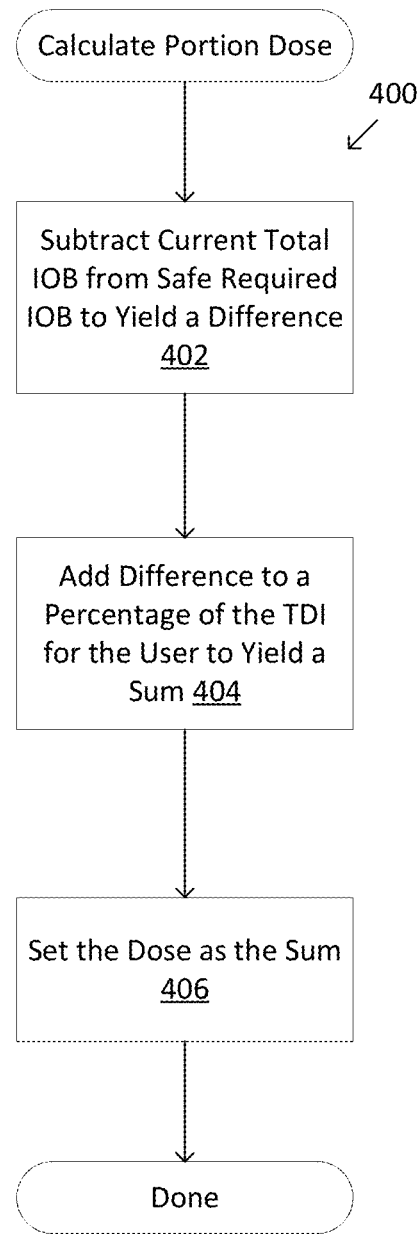
FIG. 4 depicts a flowchart of illustrative steps that may be performed in exemplary embodiments to calculate a dose for a portion of the drug bolus.

FIG. 4 depicts a flowchart 400 of illustrative steps that may be performed in exemplary embodiments to calculate a dose for a portion of the insulin bolus, in particular for the first portion. At 402, the current total Insulin on Board (IOB) for the user 108 may be subtracted from a safe required IOB to yield a difference. The total IOB includes all of the basal and bolus insulin delivered to the user that still may affect the glucose level of the user. The safe required IOB represents an IOB level that has a safety factor built into it. At 404, the difference may be added to a preset percentage of the total daily insulin (TDI) for the user 108. TDI may be the total of all insulin, basal and bolus, that is delivered to the user 108 in a day. The preset percentage may range, for example, between 3 to 8 percent of TDI. The sum reflects a percentage of TDI plus any extra insulin required to reach the safe required IOB level for the user 108. At 406, the dose for the portion, in particular the first portion, of the insulin bolus may be set as the sum. This may be expressed as:

meal dose=$x$ % TDI+safe Required IOB−Current Total IOB.

Accordingly, in some embodiments, the first portion is determined by determining a safe required IOB and determining a current total IOB, and adding the safe required IOB to a fraction of the total daily insulin and subtracting the current Total IOB therefrom. In some embodiments, the fraction of the total daily insulin is calculated as the total daily insulin for the user multiplied by a meal factor, wherein the meal factor is between about 1% to about 10%, more specifically 3% to 8%. Some user's may prefer having at minimum always delivered to feel safer when consuming a meal. Accordingly, in some embodiments, the first portion may be at least between about 0.3% to about 3% of the TDI, more specifically at least between about 0.5% to about 1.5% of the TDI and in particular at least about 0.8% to about 1.2% of the TDI. In some embodiments, the first portion may be at most between about 0.3 Units to about 3 Units, more specifically between about 0.5 Units to about 1.5 Units and in particular between about 0.8 Units to about 1.2 Units of insulin.

Figure 5:
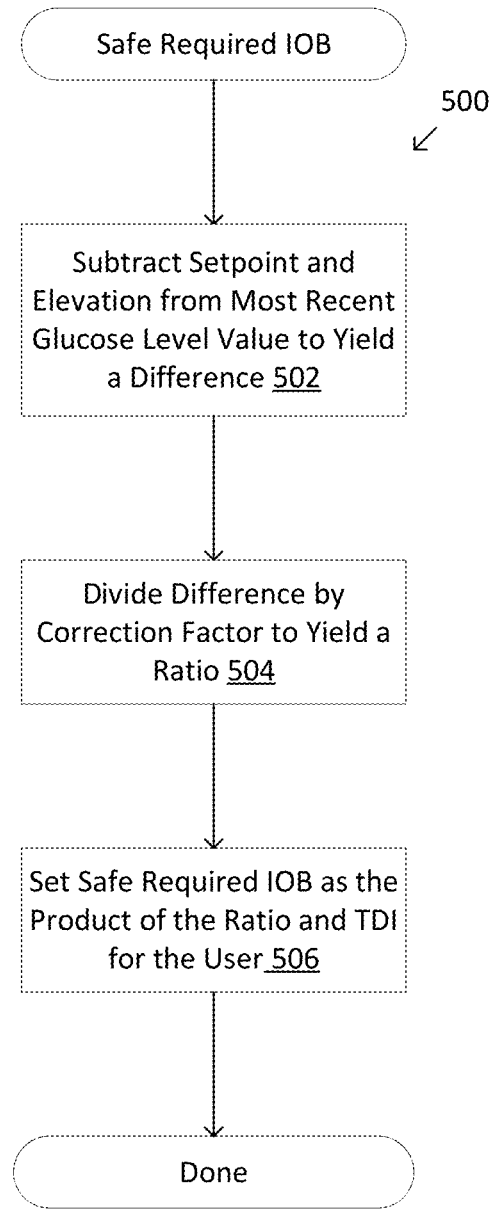
FIG. 5 depicts a flowchart of illustrative steps that may be performed tin exemplary embodiments to determine safe required drug, such as insulin, on board, or IOB.

FIG. 5 depicts a flowchart 500 of illustrative steps that may be performed to determine safe required IOB. A suitable equation for calculating the safe required IOB in exemplary embodiments is:

$$\text{Safe Required } IOB = \left(\frac{\text{Current } BG - (\text{Setpoint} + \text{Elevation})}{\text{Correction Factor}}\right) * TDI$$

and the flowchart 500 depicts steps for calculating the safe required IOB per this formula. Accordingly in some embodiments, the safe required IOB is calculated by calculating a first value as subtracting from the current glucose level value for the user the sum of the setpoint and the elevation. Then, calculating the safe required IOB by calculating a second value by dividing the first value by the user's correction factor and multiplying the second value with the user's TDI. At 502, the setpoint for the drug delivery device 102 and an elevation value are subtracted from the current glucose level value for the user 108. The resulting difference captures the difference between a glucose level value and an elevated value that is a setpoint plus an elevation amount. The setpoint may be, for example, 120 mg/dL, and the elevation may be a value such as 30 mg/dL. In some embodiments, the setpoint is between about 100 mg/dL to about 140 mg/dL, more specifically between about 110 mg/dL to about 130 mg/dL and in particular between about 115 mg/dL to about 120 mg/dL. In some embodiments, the elevation is between about 10 mg/dL to about 50 mg/dL, more specifically between about 20 mg/dL to about 40 mg/dL and in particular between about 25 mg/dL to about 35 mg/dL. The elevation may act a safety factor, which results in a lower insulin delivery to prevent hypoglycemia following insulin delivery. At 504, the difference may be divided by a correction factor to yield a ratio. At 506, the safe required IOB is set as the product of the ratio and the TDI for the user 108.

Figure 6:
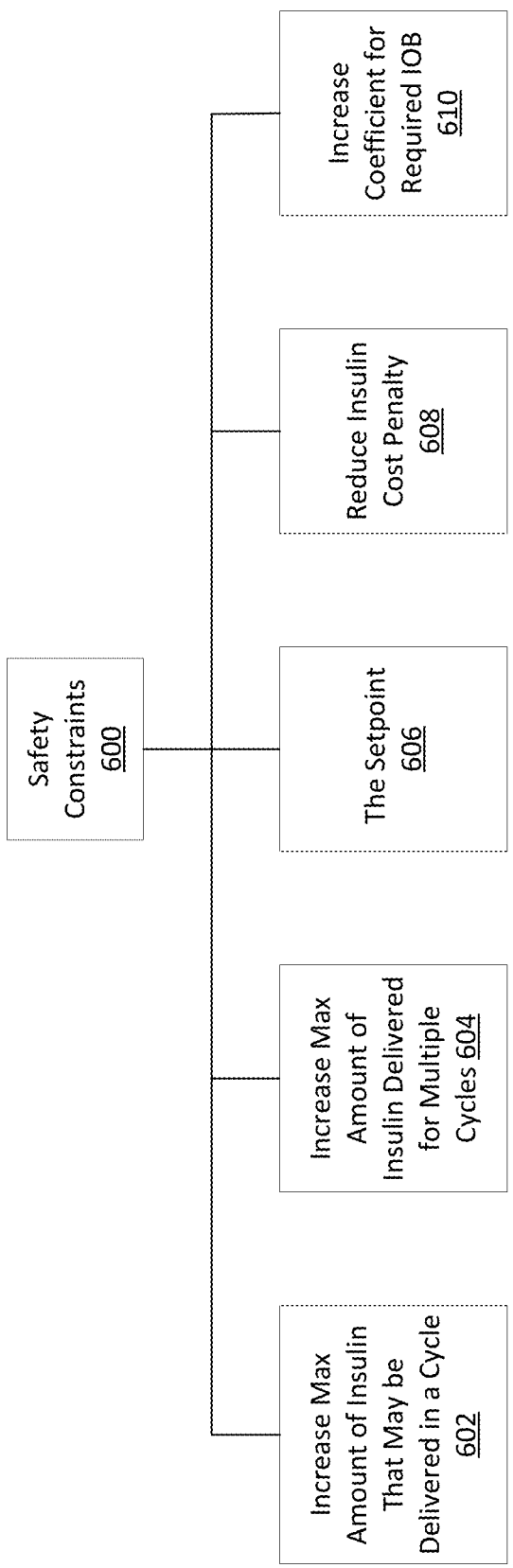
FIG. 6 depicts example of safety constraints that may be relaxed in exemplary embodiments.

With reference to FIG. 2, at 210, the first portion of the insulin bolus may be delivered to the user 108 by the insulin delivery device 102. At 212, the relaxation of one or more safety constraints may start during the next cycle after meal detection. The relaxation of one or more safety constraints may enable more insulin to be delivered as basal insulin deliveries during a relaxation period. The relaxation period may last, for example, a time frame of 6 cycles. FIG. 6 depicts example of safety constraints that may be relaxed in exemplary embodiments. The maximum amount of insulin that may be delivered in a cycle 602 is a safety constraint that may be relaxed. For instance, the maximum amount of insulin that may be delivered in a cycle may be a multiple of the ideal basal delivery amount per cycle, and the relaxing may cause the multiple to increase. Another safety constraint that may be relaxed is the maximum amount of insulin that may be delivered over multiple cycles 604. The relaxing may simply increase this maximum. The set point 606, also known as the "target," for the control application 116 or 120 is a safety constraint. The set point 606 may be lowered as part of the relaxing of constraints. For example, the greater of the current setpoint minus 20 or the fixed value of 90 mg/dL may be chosen as the new setpoint in some exemplary embodiments. In embodiments, the fixed value may be between about 70 mg/dL to about 110 mg/dL, more specifically between about 80 mg/dL to about 100 mg/dL and in particular between about 85 mg/dL to about 95 mg/dL. A further safety constraint is the cost component for insulin 608 (i.e., insulin cost). This penalty for excess insulin delivery may be decreased as part of the relaxing. A typical cost function for insulin delivery is:

$$J(I_{rec})Q(f(I_{rec})-G_{target})^n + R(I_{rec}-I_b)^m$$

where J is the total penalty, $I_{rec}$ is the current recommended insulin delivery being assessed for the total penalty, Q is the coefficient of the glucose excursions, $f(I_{rec})$ is any generic function to associate this recommended insulin delivery with a corresponding expected glucose value, $G_{target}$ is the current control target, R is the coefficient for insulin excursions, $I_b$ is the current baseline insulin delivery, and n and m are generic coefficients representing any scaling of the penalties for glucose and/or insulin excursions. The control application 116 or 120 may choose basal doses based on choosing a basal dose with a best (i.e., lowest) cost. The insulin cost is captured by $R(I_{rec}-I_b)^m$, and the coefficient R may be modified to relax the constraint.

At 214, the steps of FIG. 4 are repeated with an updated total IOB and updated safe required IOB given the new glucose level value and given the first portion of the insulin bolus having been delivered. Once the dose, in particular for the second portion, is determined, the second portion of the insulin bolus may be delivered at 216. In some embodiments, the second portion is determined 1 to 5 cycles, more specifically 1 to 3 cycles after the determination of the first portion, in particular during the cycle directly after the cycle at which the first portion was determined. In some embodiments, the second portion is determined per the same calculation as the first portion, at a cycle following the calculation of the first portion, in particular the cycle following the cycle at which the first portion was determined, wherein the current total IOB, the safe required IOB and the blood glucose value are updated to the cycle following the calculation. Accordingly, in some embodiments, the second portion is determined by determining a safe required IOB (for the cycle at which the second portion is determined) and determining a current total IOB (for the cycle at which the second portion is determined), and adding the safe required IOB (for the cycle at which the second portion is determined) to a fraction of the total daily insulin and subtracting the current Total IOB (for the cycle at which the second portion is determined) therefrom. In some embodiments, the fraction of the total daily insulin is calculated as the total daily insulin for the user multiplied by a meal factor, wherein the meal factor is between about 1% to about 10%, more specifically 3% to 8%.

Figure 7:
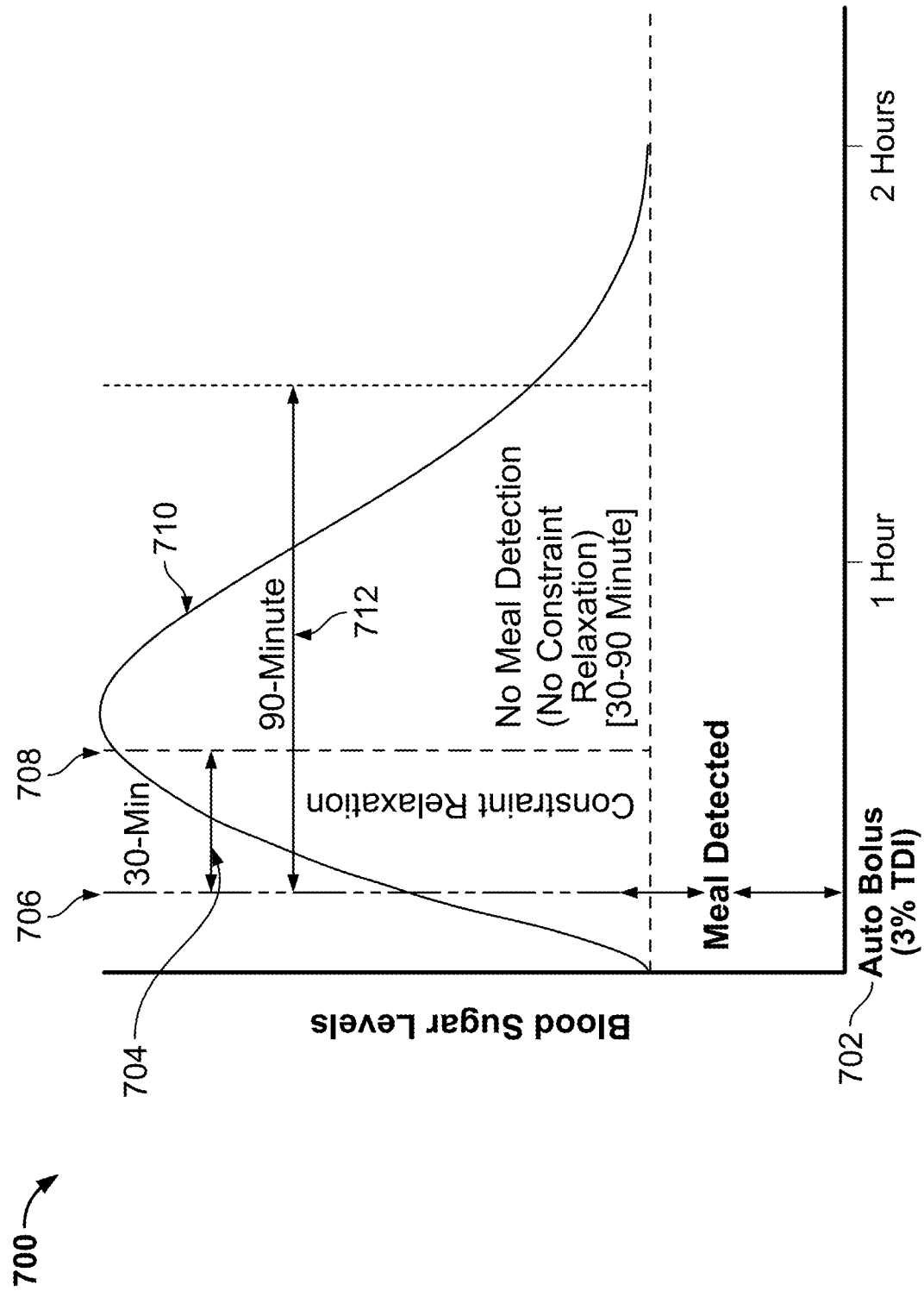
FIG. 7 depicts an illustrative plot for an exemplary AutoBolus delivery in exemplary embodiments.

FIG. 7 depicts an illustrative plot 700 for an exemplary AutoBolus delivery. The plot 700 shows that a meal is detected at time 702. The first portion of the insulin bolus may be delivered at that time and may be followed shortly (e.g., the next cycle) by delivery of the second portion. The safety constraints may be relaxed immediately for a 30 minute period 704 between times 706 and 708. The plot 700 also shows a curve 710 of the glucose level values for the user 108 over time. As is discussed below, there may be a cool down period of, for example, 90 minutes as indicated by arrow 712 after the insulin bolus is delivered. During the cool down period, there may be no meal detection so no additional boluses can be automatically delivered via the AutoBolus mechanism.

Figure 8:
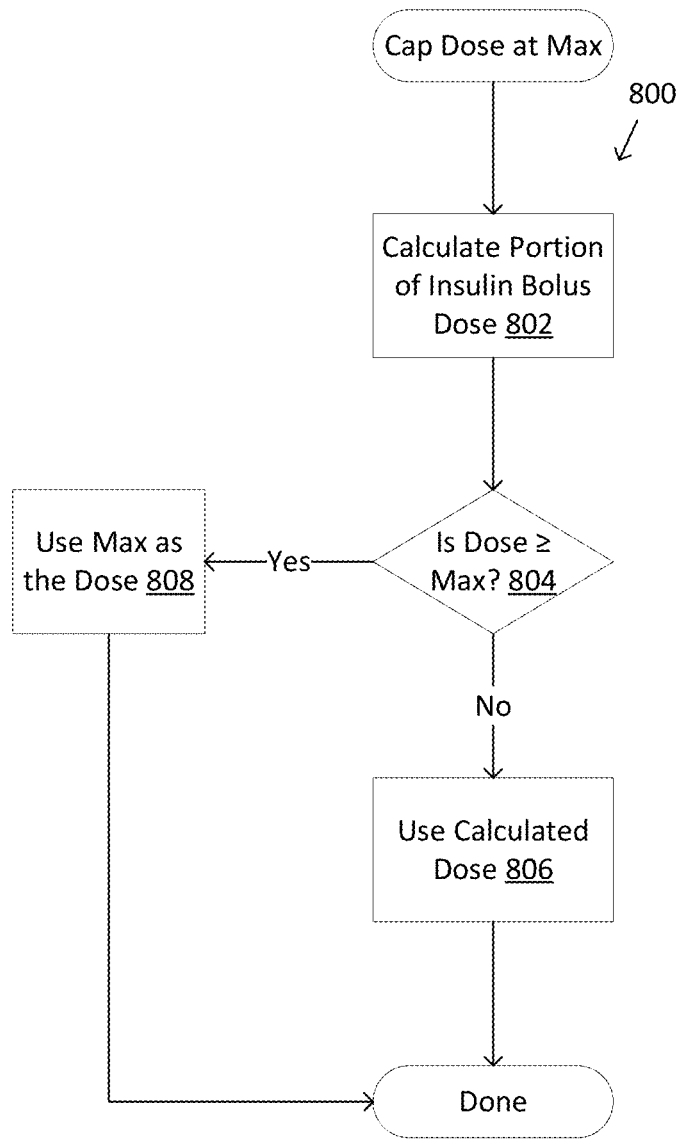
FIG. 8 depicts a flowchart of illustrative steps that may be performed in exemplary embodiments in capping drug bolus portion doses.

There are alternatives for determining the doses for the portions of the insulin bolus that differ from the approach discussed above. In some exemplary embodiments the dose for each portion of the insulin bolus may be capped. FIG. 8 depicts a flowchart 800 of illustrative steps that may be performed in exemplary embodiments in capping the doses. At 802, the dose for the portion of insulin bolus may be calculated such as described above. The dose may be compared to a maximum, such as 1 unit of insulin, that serves as a cap at 804. If the dose is greater than or equal to the cap, then the maximum may be used as the dose that ultimately may be delivered at 808. If not, the calculated dose may be used as the dose that may be delivered.

Figure 9:
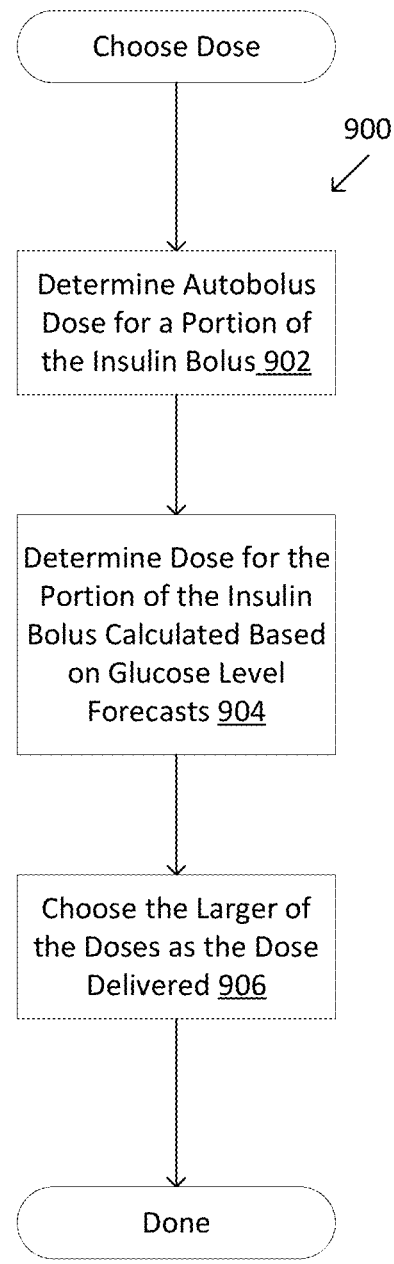
FIG. 9 depicts a flowchart of illustrative steps that may be performed in exemplary embodiments to choose among doses for a portion of an drug bolus.

In other exemplary embodiments a dose is chosen among options. FIG. 9 depicts a flowchart 900 of illustrative steps that may be performed in exemplary embodiments to choose among options. At 902, the dose may be determined for the AutoBolus delivery as described above relative to FIG. 4. At 902, a dose may be determined for the portion of the insulin bolus based on glucose level forecasts. For instance, the insulin delivery device 102 may include logic in the control application 116 that determines what bolus dose is needed to bring the glucose level of the user 108 into an acceptable range given the current glucose level of the user 108, the meal consumption and glucose level trends. At 906, the larger of the two determined doses may be chosen for the portion of the insulin bolus. It is presumed that both dose sizes are safe, and hence, the larger dose may be chosen to more quickly bring the glucose level values of the user 108 into an acceptable range.

Figure 10:
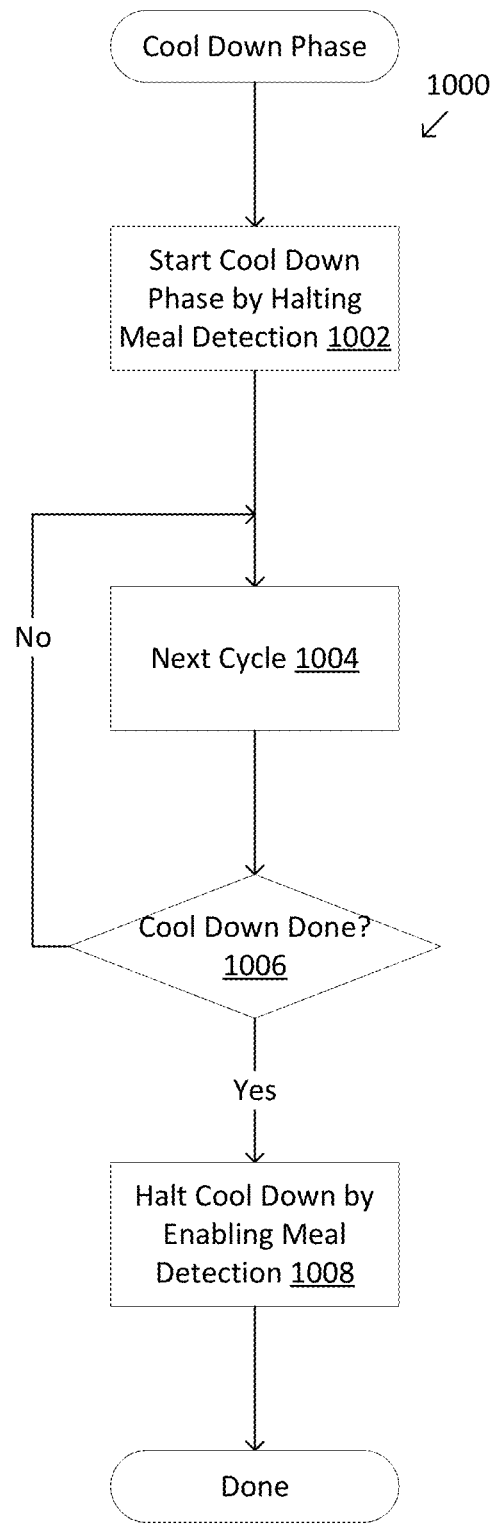
FIG. 10 depicts a flowchart of illustrative steps that may be performed in exemplary embodiments for a cool down period.

As was mentioned above, a cool down period may be provided. The cool down period helps to prevent excessive bolusing that may cause the glucose level of the user 108 to crash or to reach hypoglycemic levels or more generally, undesirably low levels. In some embodiments, the hypoglycemic level may be defined as blood glucose level between about between about 40 mg/dL to about 80 mg/dL, more specifically between about 50 mg/dL to about 70 mg/dL and in particular between about 55 mg/dL to about 65 mg/dL. The cool down period may be a fixed number of cycles, such as 12-18 cycles (i.e., with 5 minute cycles, the cool down period lasts 1 hour to 1.5 hours). In some embodiments, the cool down period has fixed number of cycles, wherein the number of cycles is between about 3 cycles to about 180 cycles, more specifically 6 cycles to about 60 cycles, and in particular between about 10 cycles to about 20 about cycles. In some embodiments, each cycle has a length between about 30 seconds to about 30 minutes, more specifically between about 1.5 minutes to about 10 minutes and in particular between about 3 minutes to about 9 minutes. FIG. 10 depicts a flowchart 1000 of illustrative steps that may be performed in exemplary embodiments for the cool down period. At 1002, the cooldown period may be entered due to delivery of an insulin bolus. The cool down period may be realized by halting meal detection and thus, halting any AutoBolus insulin deliveries. At 1004, time progresses until the next cycle is reached. At 1006, a check may be made whether the cool down period is done. If not, the process may repeat waiting until the next cycle is reached at 1004. If the end of the cool down period is reached, at 1008, the cool down period may be halted by enabling meal detection. It should be appreciated that means other than turning on and off meal detection may be used to enable and disable the AutoBolus capability.

Figure 11:
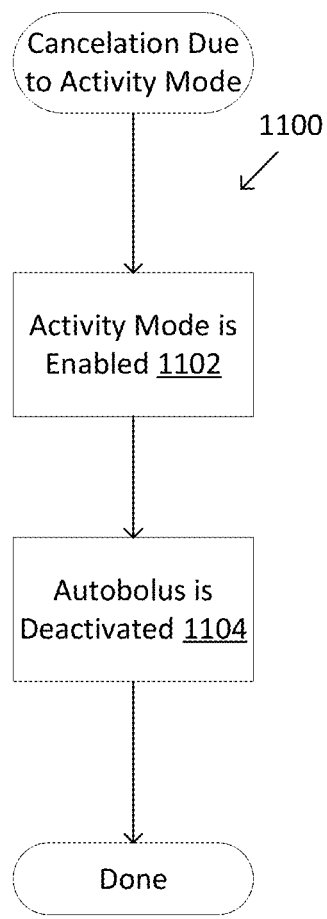
FIG. 11 depicts a flowchart of illustrative steps that may be performed in exemplary embodiments to halt the Auto-Bolus capability.

The AutoBolus capability may also be deactivated when the user exercises to prevent the user from experiencing excessively low glucose levels. FIG. 11 depicts a flowchart 1100 of illustrative steps that may be performed in exemplary embodiments to halt AutoBolus in such instances. The insulin delivery device 102 may have an activity mode that the user 108 may select when the user 108 begins exercising or is about to exercise. At 1102, the user 108 turns on the activity mode. In some embodiments, the insulin delivery device 102 automatically detects activity, such as exercise, and triggers the activity mode. At 1106, the AutoBolus capability may be then deactivated, such as described above. The AutoBolus capability may be reactivated, in some embodiments, responsive to the activity mode being turned off.

Figure 12:
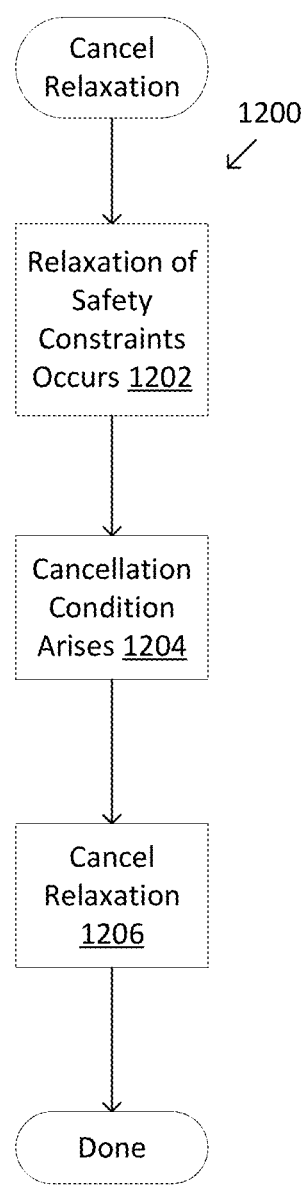
FIG. 12 depicts a flowchart of illustrative steps that may be performed in exemplary embodiments to cancel the relaxation of the one or more safety constraints.

As was mentioned above, one or more safety constraints may be relaxed responsive to the delivery of the insulin bolus. This relaxation, however, may be canceled in some exemplary embodiments if cancelation conditions arise. FIG. 12 depicts a flowchart 1200 of illustrative steps that may be performed in exemplary embodiments to cancel the relaxation of the one or more safety constraints. At 1202, the safety constraints are relaxed responsive to delivery of an insulin bolus. At 1204, a cancelation condition arises. At 1206, the relaxation of the one or more safety constraints may be canceled so that the one or more safety constraints revert to default settings or to most recently established values prior to the relaxation.

Figure 13:
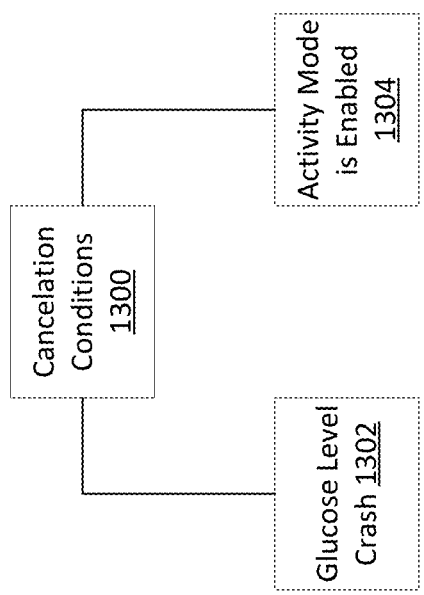
FIG. 13 depicts a couple of illustrative cancelation conditions that may be used in exemplary embodiments.

The cancelation conditions may vary. FIG. 13 depicts a couple of illustrative cancelation conditions 1300. A glucose level crash 1302 may trigger cancelation of the relaxation so as to reduce the basal insulin delivery and allow the glucose level of the user 108 to stabilize. A glucose level crash 1302 may be specified as, for example, the glucose level falling below a threshold or the glucose level of the user 108 to be dropping at more than a specified threshold rate. In some embodiments, the rate of change threshold rate may be between about −1 mg/dL/min to about −10 mg/dL/min, more specifically between about −2 mg/dL/min to about −6 mg/dL/min and in particular −2.5 mg/dL/min to about −4 mg/dL/min. Alternatively or additionally, in some embodiment a glucose level crash 1302 may be specified as the glucose level falling for at least three cycles. In some embodiments, the glucose level crash may be specified if the rate of change threshold rate is exceeded between two subsequent cycles and/or between three subsequent cycles. In some embodiments, a glucose level crash may be determined if the of change threshold rate is exceeded between two subsequent cycles or three subsequent cycles, wherein the rate of change threshold for the three subsequent cycles is lower when determining a glucose level crash over three subsequent cycles compared too over two subsequent cycles, more specifically between about 20% to about 70% lower, in particular between about 40% to about 60% lower. In some embodiments, a glucose level crash may be specified if the glucose level decreases between four subsequent cycles. Another cancelation condition may be that an activity mode is enabled 1304. The exercise performed by the user when in activity mode, or in other words when the user is exercising, will cause the glucose level of the user to drop 108, so there is a risk that the potential greater insulin delivery due to the relaxed safety constraints may cause the glucose level of the user to drop to too low of a level. Hence, cancelation of the relaxation is warranted.

Figure 14A:
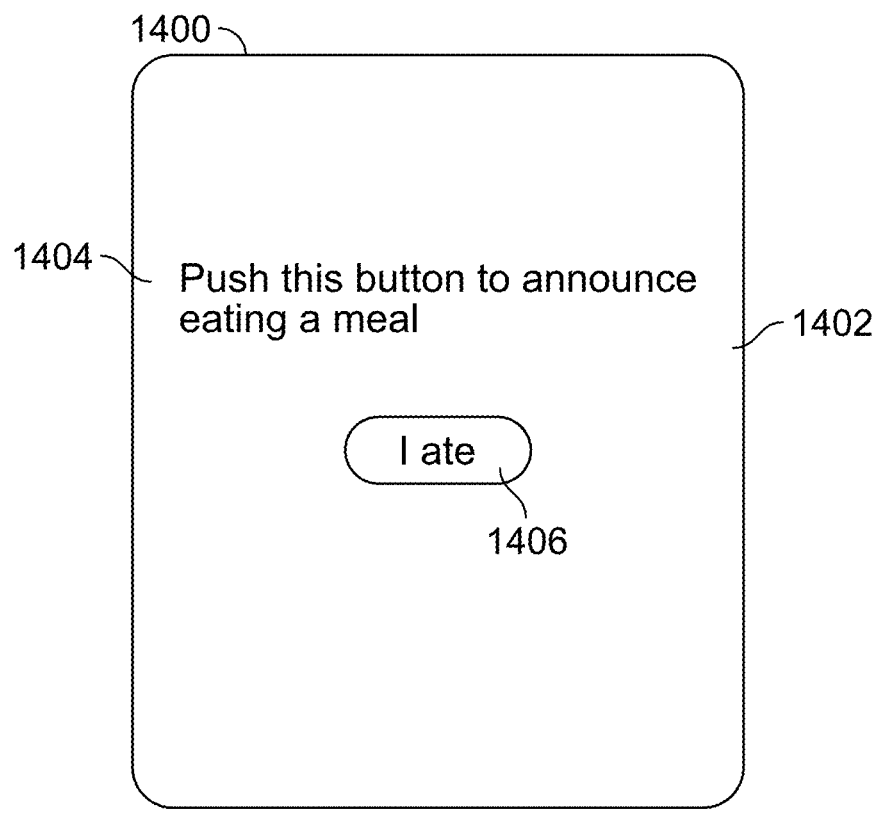
FIG. 14A depicts an example of a user interface button on a management device that may be activated by a user to announce eating a meal.
Figure 14B:
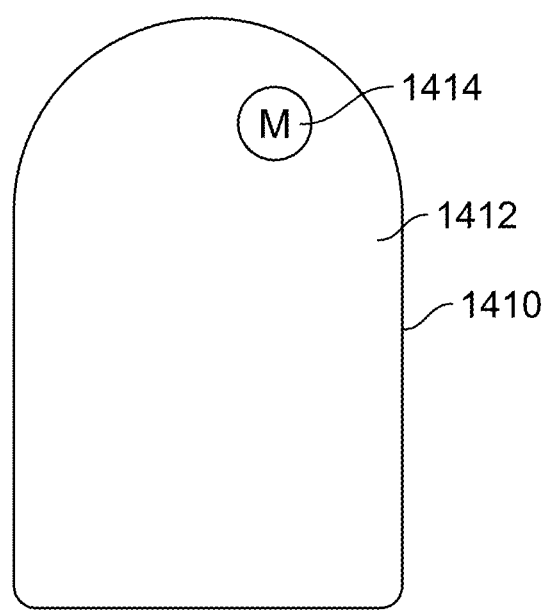
FIG. 14B depicts an illustrative drug delivery device of an exemplary embodiment that has a button on its housing that may be depressed by a user to announce eating a meal.
Figure 14C:
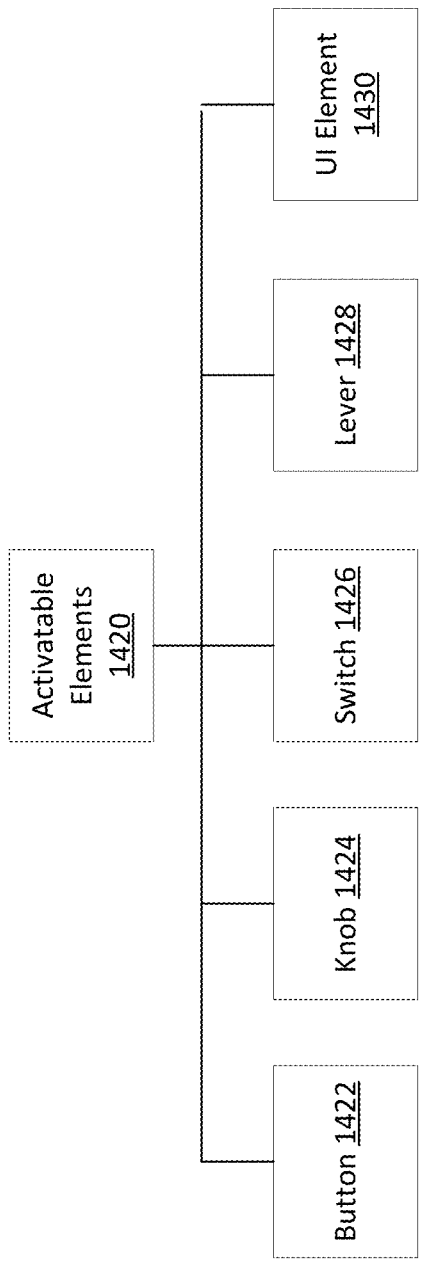
FIG. 14C depicts a number of illustrative activatable elements that may be activated by a user to announce eating a meal.

As was mentioned above, the delivery of an insulin bolus and the relaxation of safety constraints for a period may also be triggered by the user 108 activating an element on the drug delivery device 102 or the management device to announce to a meal. For example, as shown in FIG. 14A, the management device 1400 may include a display 1402. The display 1402 may show text that instructs the user 108 to push a button 1406 to indicate the user 108 has eaten a meal. The pushing of the button 1406 announces that the user 108 has eaten a meal and the drug delivery device may deliver a meal insulin bolus as explained below. The element that is activated to announce a meal may instead or in additionally be on the drug delivery device 102. FIG. 14B depicts a top view of a drug delivery device 1410. The top portion of the housing 1412 may include a mechanical, electromechanical, or electrical button 1414 (e.g., a physical or alternatively a "soft" button may be used) that may be depressed or touched to announce that the user has eaten a meal or is about to eat a meal. Settings in drug delivery device 102 may include user-adjustable settings that indicate an approximate time of when a meal will be consumed after pressing button 1414. For example, a user may set the settings to "5-minutes" meaning that the user will typically eat 5-minutes after pressing button 1414. Other types of elements may be provided for the user 108 to announce eating a meal in some embodiments. FIG. 14C depicts a diagram listing some of the types of elements that may be activated to announce that the user 108 has eaten a meal. The activatable elements 1420 may include a button 1422, a knob 1424, a switch 1426, a lever 1428, or a user interface (UI) element 1430. It should be appreciated that other varieties of activatable elements may be used and that the depiction in FIG. 14C is not intended to be exhaustive.

Figure 15:
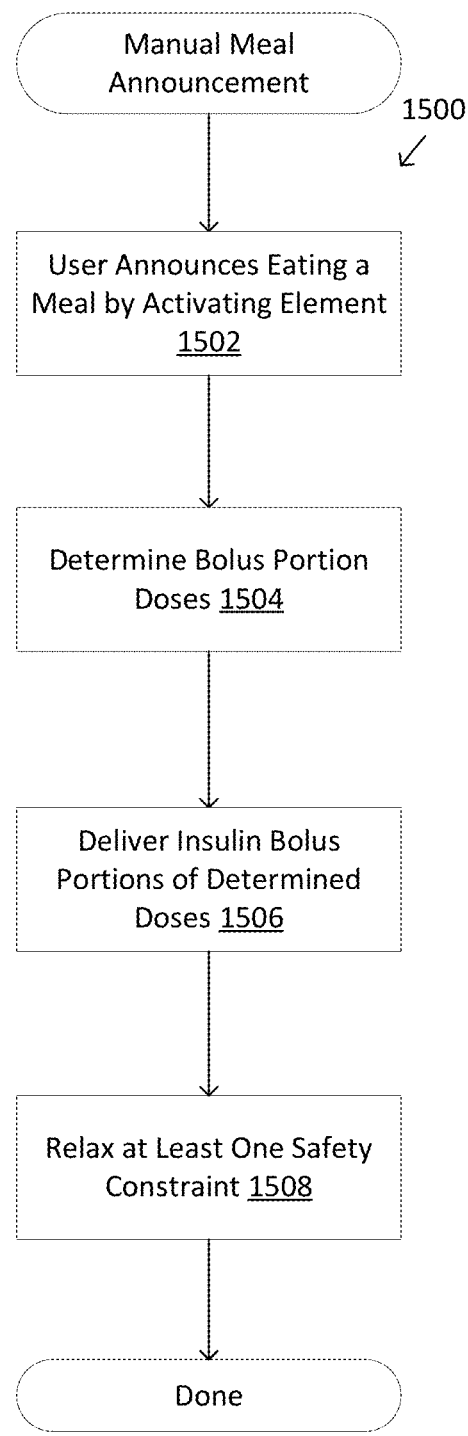
FIG. 15 depicts a flowchart of illustrative steps that may be performed in exemplary embodiments to deliver a meal drug bolus and relax at least one safety restraint responsive to activation by a user of an activatable element to announce eating a meal.

FIG. 15 depicts a flowchart 1500 of illustrative steps that may be performed in exemplary embodiments when the manual meal announcement approach is used. At 1502, the user 108 announces eating a meal by activating the activatable element. In response to the activation, at 1504, the drug delivery device 102 may determine the doses for portions of the insulin bolus that is to be delivered as a meal insulin bolus. This may be done as discussed above relative to FIG. 4. At 1506, the drug delivery device 102 delivers the portions of the insulin bolus as described above relative to FIG. 3. At 1508, at least one of the safety constraints is relaxed as described above.

There may be a cool down period once the portions of the insulin bolus have been delivered as described above. The relaxation of the safety constraints may be canceled as described above relative to claims 12 and 13.

Figure 16A:
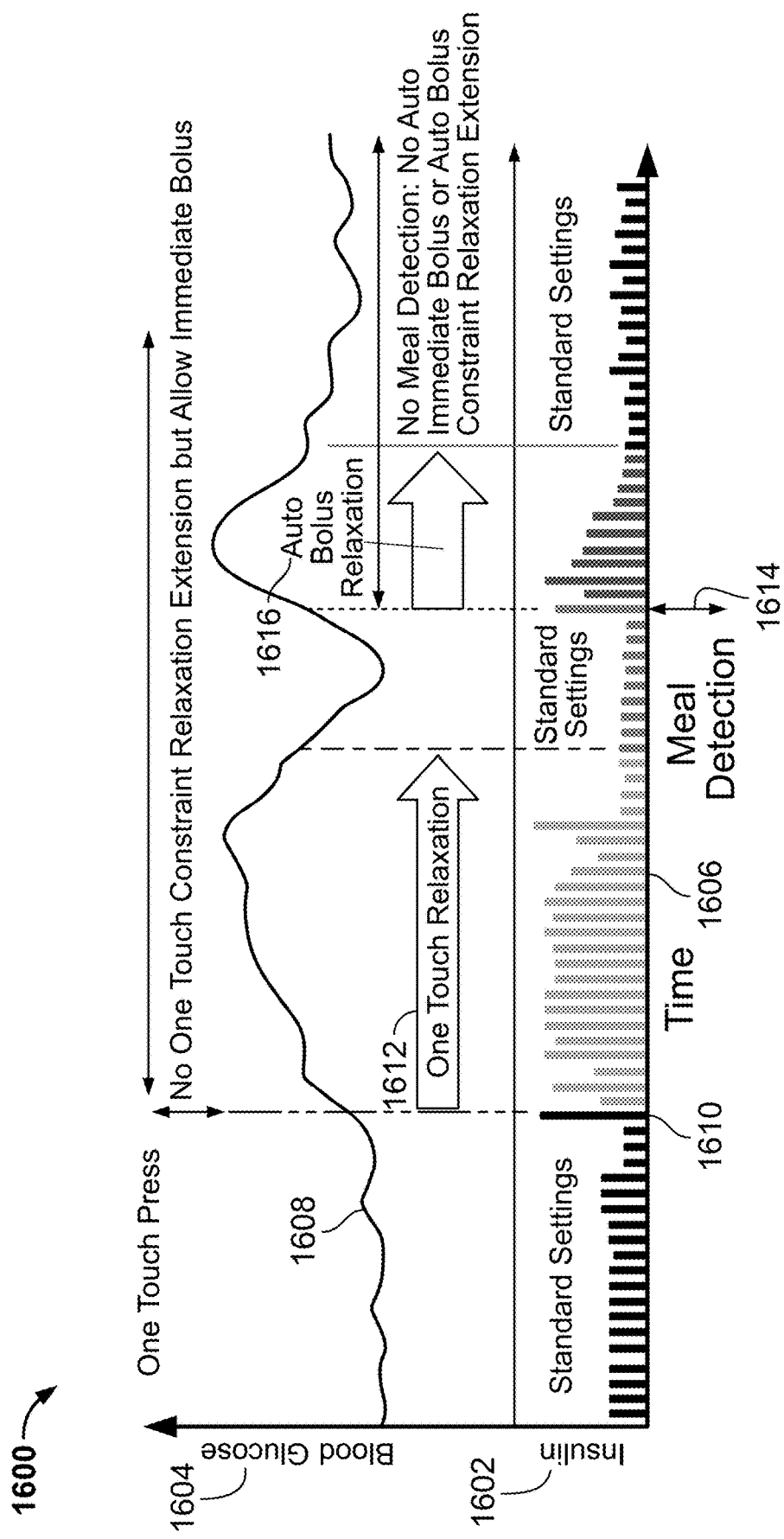
FIGS. 16A, 16B, and 16C depict plots that illustrate cooperation of the AutoBolus capability, and the manual meal announcement induced meal drug bolus capability of exemplary embodiments.

In some exemplary embodiments, the AutoBolus capability and the manual meal announcement may be used together. The drug delivery device 102 may take measures to ensure that these two approaches for identifying meals and delivering meal insulin boluses in response are compatible. FIG. 16A depicts a plot 1600 of operation when the AutoBolus and meal announcement effects do not overlap in their timing. The plot 1600 plots insulin delivery amounts 1602 over time 1606 and glucose levels 1604 of the user over time 1606. Curve 1608 of the glucose levels is shown. The plot 1600 also shows where standard safety settings are in effects as indicated by "standard settings" along the time axis. In this depiction, at time 1610, the user 108 activates an activatable element to announce eating a meal. The drug delivery device 102 determines the doses for a first and second portions of an insulin bolus and delivers the first and second portions of the insulin bolus as described above. At least one of the safety constraints is relaxed from the "standard settings" for the relaxation period as indicated by arrow 1612. After relaxation period ends the safety constraints are no longer relaxed. A meal is detected at time 1614. The drug delivery device determines doses for the first and second portions of an insulin bolus and delivers them to the user 108. At least one safety constraint is relaxed for the relaxation period as indicated by arrow 1616. Once the relaxation period ends, the one or more safety constraints that were relaxed are no longer relaxed.

Figure 16B:
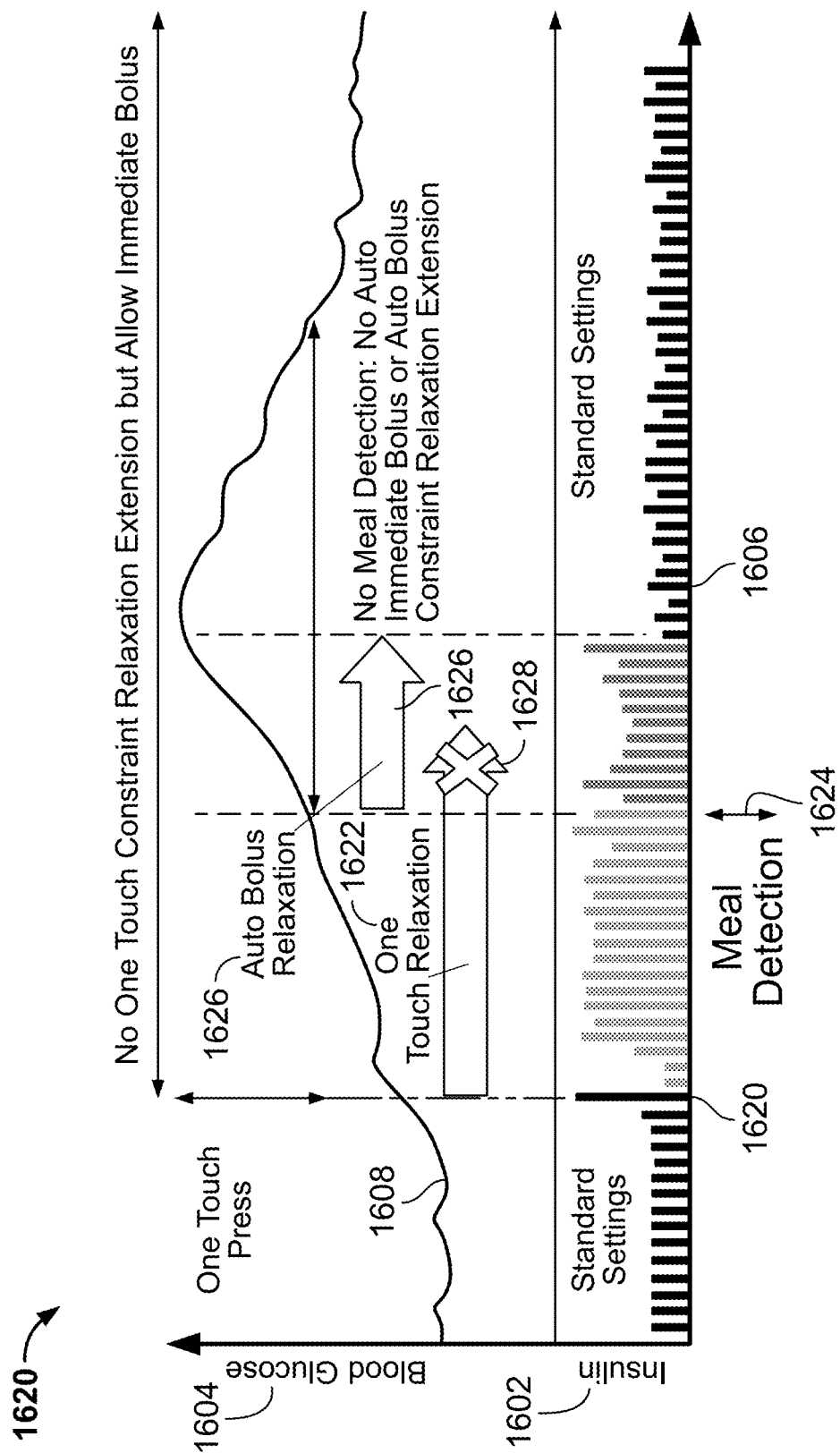

FIG. 16B depicts a plot 1620 when the AutoBolus capability is triggered while the at least one safety constraint is relaxed from the "standard settings" following insulin bolus delivery responsive to a manual meal announcement. In the depicted instance, at time 1620, the user 108 announces a meal by activating an activatable element. The drug delivery device 102, determines doses for first and second portions of a meal insulin bolus and delivers the first and second portions to the user 108. At least one safety constraint is relaxed over a period indicated by arrow 1622. At time 1624, a meal is detected. The Autobolus capability delivers first and second portions of an insulin bolus in response to the meal detection. At least one safety constraint is relaxed by the AutoBolus capability for a relaxation period indicated by arrow 1626. The relaxation of at least one safety constraint resulting from the manual meal announcement is terminated as indicated by the "X" 1628. The reversion to the "standard settings" after the relaxation period indicted by arrow 1626 is shown.

Figure 16C:
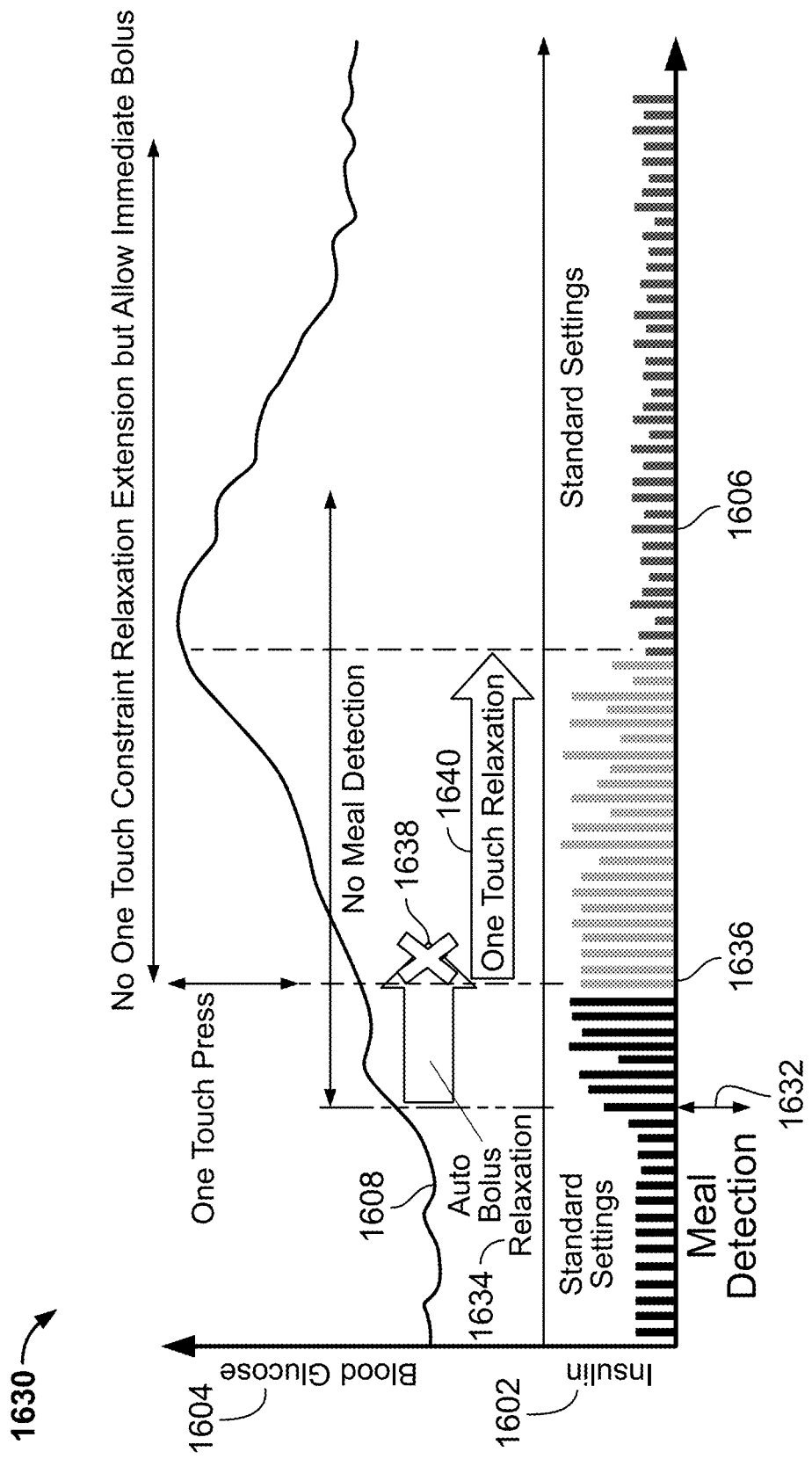

FIG. 16C depicts a third plot 1630 that is like those of FIGS. 16A and 16B. However, in this example plot, at time 1632, a meal is detected. In response, the AutoBolus capability delivers first and second portions of a meal insulin bolus and relaxes at least one constraint of the "standard settings" for a period that is indicated by arrow 1634. At time 1636, the user 108 activates an activatable element to announce eating a meal. First and second portions of a meal insulin bolus are delivered to the user 108 by the drug delivery device 102. At least one safety constraint is relaxed in response for a relaxation period that is indicated by arrow 1640. The previous relaxation of at least one safety constraint resulting from the AutoBolus insulin bolus delivery is halted as indicated by the "X" 1638. The "standard settings are again employed after the relaxation period 1640 ends.

The present disclosure furthermore relates to computer programs comprising instructions (also referred to as computer programming instructions) to perform the aforementioned functionalities. The instructions may be executed by a processor. The instructions may also be performed by a plurality of processors for example in a distributed computer system. The computer programs of the present disclosure may be for example preinstalled on, or downloaded to the medicament delivery device, management device, fluid delivery device, e.g. their storage. The computer program may calculate the first portion and second portion to be delivered.

While exemplary embodiments have been described herein, various changes in form and detail may be made without departing from the intended scope of the attached claims.

Although the present invention is defined in the attached claims, it should be understood that the present invention can also (alternatively) be defined in accordance with the following embodiments:

1. A drug delivery system for delivery of drug to a user, comprising:
   a storage of drug;
   a needle or cannula for piercing the skin of the user to deliver the drug from the storage;
   a fluid path for the drug between the storage to the needle or cannula;
   a non-transitory computer-readable storage medium storing computer programming instructions; and
   a processor configured to execute the computer programming instructions, wherein executing the computer programming instructions causes the processor to:
   constrain delivery of the drug to the user,
   receive glucose level values for the user,
   determine whether the user has eaten based on the received glucose level values for the user,
   provide an auto bolus capability to deliver a first portion of an drug bolus to the user responsive to the processor determining that the user has eaten, and
   relax at least one drug safety constraint for a period following the delivery of the first portion of the drug bolus so that larger doses of automated drug deliveries may be delivered subject to the relaxed at least one drug safety constraint.

2. The drug delivery system of embodiment 1, wherein the executing of the computer programming instructions further causes the processor to deliver a second portion of the drug bolus.

3. The drug delivery system of embodiment 2, wherein the executing of the computer programming instructions further causes the processor to determine a dose for the second portion of the drug bolus.

4. The drug delivery system of embodiment 3, wherein the second portion of the dose is determined based at least in part in a most recent received glucose level value and drug on board for the user.

5. The drug delivery system of embodiment 2, wherein the executing of the computer programming instructions further causes the processor to prevent delivery of another drug bolus during a cool down period following delivery of the second portion of the drug bolus.

6. The drug delivery system of embodiment 5, wherein executing of the computer programming instructions further causes the processor to cancel the auto bolus capability if an activity mode is set wherein the activity mode being set indicates that the user is active or going to be active shortly, or if the user is in the cool down period.

7. The drug delivery system of embodiment 1, wherein the executing of the computer programming instructions further causes the processor to cancel the relaxing of the at least one drug delivery constraint if at least one cancelation condition other than the expiration of the period is satisfied.

8. The drug delivery system of embodiment 1, wherein the at least one cancelation condition includes at least one of differences between consecutively received blood glucose values for the user exceeding respective thresholds or an activity mode is set wherein the activity mode being set indicates that the user is active or going to be active shortly.

9. A drug delivery system for delivery of a drug to a user, comprising:
   a storage of the drug;
   a needle or cannula for piercing the skin of the user to deliver the drug from the storage;
   a fluid path for the drug between the storage to the needle or cannula;
   a non-transitory computer-readable storage medium storing computer programming instructions; and
   a processor configured to execute the computer programming instructions, wherein executing the computer programming instructions causes the processor to:
   constrain delivery of the drug to the user per current drug safety constraints;
   receive an indication of a user request to deliver a drug bolus to the user,
   responsive to the received request, deliver a first portion of the drug bolus to the user, and
   relax at least one of the current drug safety constraints for a period following the delivery of the first portion of the drug bolus so that larger doses of basal drug deliveries may be delivered if needed without being subject to the at least one of the current drug safety constraints that were relaxed.

10. The drug delivery system of embodiment 9, further comprising an element that may be activated by the user to request delivery of the drug bolus.

11. The drug delivery system of embodiment 9, wherein the element is one of a button, a knob, a switch, or a lever.

12. The drug delivery system of embodiment 9, wherein the drug delivery device further comprises a user interface and the element is a user interface element.

13. The drug delivery system of embodiment 9, wherein the executing of the computer programming instructions further causes the processor to deliver a second portion of the drug bolus.

14. The drug delivery system of embodiment 9, wherein the executing of the computer programming instructions further causes the processor to determine a dose for the second portion of the drug bolus.

15. The drug delivery system of embodiment 9, wherein the executing of the computer programming instructions further causes the processor to prevent delivery of another drug bolus during a cool down period following delivery of the second portion of the drug bolus.

16. The drug delivery system of embodiment 9, wherein the executing of the computer programming instructions further causes the processor to cancel the relaxing of the at least one drug safety constraint if differences between consecutively received blood glucose values for the user exceed respective thresholds or if an activity mode is set wherein the activity mode being set indicates that the user is active or going to be active shortly.

17. A drug delivery device, comprising:
   a drug reservoir storing a drug;
   a needle or cannula for piercing skin of a patient, said needle or cannula being hollow so as to serve as a conduit for delivering the drug to the user;
   a non-transitory computer-readable storage storing computer programing instructions for controlling operation of the drug delivery device;
   a processor for executing the computer programming instructions to cause the processor to:
   constrain delivery of the drug to the user per current drug delivery constraints;
   deliver a first portion of the drug bolus to the user, and relax at least one of the current drug safety constraints for a period following the delivery of the first portion of the drug bolus so that larger doses of basal drug deliveries may be delivered if needed without being subject to the at least one current drug safety constraints that were relaxed.

18. The drug delivery device of embodiment 17, wherein multiple of the current drug safety constraints are relaxed.

19. The drug delivery device of embodiment 17, wherein the drug safety constraints include at least one of a maximum amount of drug that can be delivered to the user from the drug delivery device in an operational cycle of the drug delivery device, a maximum amount of drug that can be delivered to the user from the drug delivery device in a specified number of operational cycles of the drug delivery device, a current setpoint for glucose level of the user, a maximum level of drug on board for the user, and a penalty amount in a cost function for extra drug delivery.

20. The drug delivery device of embodiment 17, wherein the executing of the computer programming instructions further causes the processor to deliver a second portion of the drug bolus at a fixed time after delivery of the first portion of the drug bolus.

21. A method performed by a processor of a drug delivery system, wherein the method comprises:
   receiving glucose level values for the user, and/or other analyte level values, determining whether the user has eaten based on the received analyte level values for the user, an auto bolus capability to determine a first portion of a drug bolus to be delivered to the user responsive to determining that the user has eaten,
   determining that the drug delivery system has delivered the first portion to the user, and relaxing at least one drug safety constraint for a period following the determination that the first portion of the drug bolus has been delivered, wherein relaxing the at least one drug safety constraint allows determination of larger doses of basal drug deliveries to be delivered if needed without being subject to the at least one drug safety constraints that were relaxed.

22. The method of embodiment 21, wherein the method further comprises determining a dose for the second portion of the drug bolus to be delivered to the user.

23. The method of embodiment 22, wherein the second portion of the dose is determined based at least in part on a most recent received analyte level value and drug on board for the user.

24. The method of embodiment 22 or 23, wherein the method further comprises determining that the second portion of the drug bolus has been delivered.

25. The method of embodiment 24, wherein the method further comprises preventing delivery of another drug bolus during a cool down period following the determination that the second portion of the drug bolus has been delivered and/or sending instructions to the drug delivery device indicating that another drug bolus shall not be delivered within the cool down period following the determination that the second portion of the drug bolus has been delivered.

26. The method of any one of embodiments 21 to 25, wherein the method further comprises canceling the auto bolus capability if an activity mode is set wherein the activity mode being set indicates that the user is active or going to be active shortly or if the user is in the cool down period.

27. The method of any one of embodiments 21 to 26, wherein the method further causes the processor to cancel the relaxing of the at least one drug delivery constraint if at least one cancelation condition other than the expiration of the period is satisfied.

28. The method of embodiment 26, wherein the cancelation condition(s) may include at least one of a difference between consecutively received blood glucose values for the user that exceeds a threshold or an activity mode is set wherein the activity mode being set indicates that the user is active or going to be active shortly.

29. A method performed by a processor of a drug delivery system, wherein the method comprises:
   receiving an indication of a user request to deliver a drug bolus immediately to the user,
   responsive to the received request, determining a first portion of the drug bolus to be delivered the user,
   determining that the first portion of the drug bolus has been delivered by the drug delivery system, and
   relaxing at least one of a current drug safety constraint for a period following the delivery of the first portion of the drug bolus, wherein relaxing the at least one drug safety constraint allows determination of larger doses of basal drug deliveries to be delivered if needed without being subject to the at least one drug safety constraints that were relaxed.

30. A method performed by a processor of a drug delivery system, wherein the method comprises determining a first portion of a drug bolus to be delivered the user,
   determining that the first portion of a drug bolus has been delivered by the drug delivery system, and
   relaxing at least one of the current drug safety constraints for a period following the delivery of the first portion of the drug bolus, wherein relaxing the at least one drug safety constraint allows determination of larger doses of basal drug deliveries to be delivered if needed without being subject to the at least one drug safety constraints that were relaxed.

The invention claimed is:

1. A drug delivery system for delivery of drug to a user, comprising:
   a storage for the drug;
   a needle or cannula for piercing skin of the user to deliver the drug from the storage;
   a fluid path for the drug between the storage and the needle or cannula;
   a non-transitory computer-readable storage medium storing computer programming instructions; and
   a processor configured to execute the computer programming instructions, wherein executing the computer programming instructions causes the processor to:
      constrain a dose size of the drug that is permitted to be delivered to the user by the drug delivery system in accordance with one or more drug safety constraints,
      receive glucose level values for the user,
      determine whether the user has eaten based on the received glucose level values for the user,
      provide an auto bolus capability to deliver a first portion of a drug bolus to the user responsive to the processor determining that the user has eaten, and
      modify at least one of the one or more drug safety constraints for a period following the delivery of the first portion of the drug bolus so that the dose size of automated drug deliveries by the drug delivery system that is permitted is increased.

2. The drug delivery system of claim 1, wherein the executing of the computer programming instructions further causes the processor to deliver a second portion of the drug bolus.

3. The drug delivery system of claim 2, wherein the executing of the computer programming instructions further causes the processor to determine a dose for the second portion of the drug bolus.

4. The drug delivery system of claim 3, wherein the second portion of the dose is determined based at least in part on a most recent received glucose level value and drug on board for the user.

5. The drug delivery system of claim 2, wherein the executing of the computer programming instructions further causes the processor to prevent delivery of another drug bolus during a cool down period following delivery of the second portion of the drug bolus.

6. The drug delivery system of claim 5, wherein executing of the computer programming instructions further causes the processor to cancel the auto bolus capability if an activity mode is enabled wherein the activity mode being set indicates that the user is active or going to be active shortly, or if the user is in the cool down period.

7. The drug delivery system of claim 1, wherein the executing of the computer programming instructions further causes the processor to cancel the modifying at least one of the one or more drug safety constraints if at least one cancelation condition other than the expiration of the period is satisfied.

8. The drug delivery system of claim 1, wherein the at least one cancelation condition includes at least one of differences between consecutively received blood glucose values for the user exceed respective thresholds or an activity mode is set wherein the activity mode being set indicates that the user is active or going to be active shortly.

9. An drug delivery system for delivery of a drug to a user, comprising:
   a storage for the drug;
   a needle or cannula for piercing skin of the user to deliver the drug from the storage;
   a fluid path for the drug between the storage and the needle or cannula;
   a non-transitory computer-readable storage medium storing computer programming instructions; and
   a processor configured to execute the computer programming instructions, wherein executing the computer programming instructions causes the processor to:
      constrain a dose size of the drug that is permitted to be delivered to the user by the drug delivery system in accordance with one or more drug safety constraints,
      receive an indication of a user request to deliver a drug bolus to the user,
      responsive to the received request, deliver a first portion of the drug bolus to the user, and
      modify at least one of the one or more drug safety constraints for a period following the delivery of the first portion of the drug bolus so that the dose size of basal drug deliveries by the drug delivery system that is permitted is increased.

10. The drug delivery system of claim 9, further comprising an element that may be activated by the user to request delivery of the drug bolus.

11. The drug delivery system of claim 9, wherein the element is one of a button, a knob, a switch, or a lever.

12. The drug delivery system of claim 9, wherein the drug delivery device further comprises a user interface and the element is a user interface element.

13. The drug delivery system of claim 9, wherein the executing of the computer programming instructions further causes the processor to deliver a second portion of the drug bolus.

14. The drug delivery system of claim 9, wherein the executing of the computer programming instructions further causes the processor to determine a dose for the second portion of the drug bolus.

15. The drug delivery system of claim 9, wherein the executing of the computer programming instructions further causes the processor to prevent delivery of another drug bolus during a cool down period following delivery of the second portion of the drug bolus.

16. The drug delivery system of claim 9, wherein the executing of the computer programming instructions further causes the processor to cancel the modifying of the at least one of the one or more drug safety constraints if differences between consecutively received blood glucose values for the user exceed respective thresholds or if an activity mode is set wherein the activity mode being set indicates that the user is active or going to be active shortly.

17. A drug delivery device, comprising:
   a drug reservoir for storing a drug;
   a needle or cannula for piercing skin of a patient, said needle or cannula being hollow so as to serve as a conduit for delivering the drug to the user;
   a non-transitory computer-readable storage storing computer programing instructions for controlling operation of the drug delivery device;
   a processor for executing the computer programming instructions to cause the processor to:
      constrain a dose size of the drug that is permitted to be delivered by the drug delivery device to the user in accordance with one or more drug delivery constraints,
      deliver a first portion of the drug bolus to the user, and
      modify at least one of the one or more drug safety constraints for a period following the delivery of the first portion of the drug bolus so that the dose size of basal drug deliveries that are permitted to be delivered by the drug delivery device is increased.

18. The drug delivery device of claim 17, wherein multiple of the drug safety constraints are modified.

19. The drug delivery device of claim 17, wherein the drug safety constraints include at least one of a maximum amount of drug that is permitted to be delivered to the user from the drug delivery device in an operational cycle of the drug delivery device, a maximum amount of drug that is permitted to be delivered to the user from the drug delivery device in a specified number of operational cycles of the drug delivery device, a current setpoint for glucose level of the user, a maximum level of drug on board for the user, and a penalty amount in a cost function for extra drug delivery.

20. The drug delivery device of claim 17, wherein the executing of the computer programming instructions further causes the processor to deliver a second portion of the drug bolus at a fixed time after delivery of the first portion of the drug bolus.

\* \* \* \* \*